(12) United States Patent
Rich

(10) Patent No.: US 7,354,730 B2
(45) Date of Patent: Apr. 8, 2008

(54) HIGH-THROUGHPUT ASSAY OF HEMATOPOIETIC STEM AND PROGENITOR CELL PROLIFERATION

(75) Inventor: Ivan N. Rich, Colorado Springs, CO (US)

(73) Assignee: HemoGenix, Inc., Colorado Springs, CO (US)

(*) Notice: Subject to any disclaimer, the term of this patent is extended or adjusted under 35 U.S.C. 154(b) by 472 days.

(21) Appl. No.: 10/645,077

(22) Filed: Aug. 21, 2003

(65) Prior Publication Data

US 2004/0110243 A1 Jun. 10, 2004

Related U.S. Application Data

(63) Continuation-in-part of application No. 10/059,521, filed on Jan. 29, 2002.

(60) Provisional application No. 60/404,972, filed on Aug. 21, 2002.

(51) Int. Cl.
*C12Q 1/66* (2006.01)

(52) U.S. Cl. .............. 435/8; 435/1.2; 435/2; 435/3; 435/7.2; 435/40.51; 435/40.52; 435/374; 435/375; 435/376; 435/377; 435/384; 435/385; 435/386; 435/387; 435/388; 435/372

(58) Field of Classification Search .............. 435/1.2, 435/1.3, 2, 3, 7.2, 8, 40.5, 40.52, 374–377, 435/384–388, 391, 392, 405–408, 40.51, 435/7.23, 7.24, 7.92; 436/501, 503, 17, 18, 436/63, 64, 906, 147, 813
See application file for complete search history.

(56) References Cited

U.S. PATENT DOCUMENTS

| | | | |
|---|---|---|---|
| 5,641,641 A | 6/1997 | Wood | 435/8 |
| 5,733,541 A | 3/1998 | Taichman et al. | 424/93.1 |
| 5,814,471 A | 9/1998 | Wood | 435/8 |
| 5,854,010 A | 12/1998 | Denison et al. | 435/8 |
| 6,440,407 B1* | 8/2002 | Bauer et al. | 424/85.1 |
| 6,824,973 B2* | 11/2004 | Tang et al. | 435/4 |
| 2002/0120098 A1* | 8/2002 | Bell et al. | 530/300 |

FOREIGN PATENT DOCUMENTS

| | | |
|---|---|---|
| WO | WP 92/13063 | 8/1992 |
| WO | 98/21313 | 5/1998 |

OTHER PUBLICATIONS

Crouch et al., The use of ATP Bioluminescence as a measure of Cell Proliferation and Cytotoxicity, Journal of Immunological Methods, 160: 81-88 (1993).*

(Continued)

*Primary Examiner*—Gailene Rio Gabel
(74) *Attorney, Agent, or Firm*—David G. Rosenbaum; Donna E. Becker; Rosenbaum & Associates, PC

(57) ABSTRACT

The present invention relates generally to kits that provide reagent mixes and instructions for the use thereof, in performing high-throughput assay methods that determine the proliferative status of isolated target cell populations. The methods measure the luminescent output derived from the intracellular ATP content of incubated target cells, and correlate the luminescence with the proliferative status of the cells. The present invention further relates to kits that provide reagent mixes and instructions for high-throughput assays methods for screening compounds that may modulate the proliferative status of a target cell population. The kits of the present invention and methods therein described may be used for determining the proliferative status of any isolated cell line or type. The kits and methods of the present invention address the need for rapid assays that determine the proliferative status of isolated hematopoietic stem and progenitor cells and of subpopulations of differentiated cells thereof.

48 Claims, 19 Drawing Sheets

OTHER PUBLICATIONS

"Circannual Variations Of Circadian Periodicity In Murine Colony-Forming Cells"; Aardal, Nils-Petter, Experimental Hematology, 12:61-67 (1984).

"Circadian Variations in Mouse Bone Marrow"; Aardal, N.P & Laerum, O.D., Experimental Hematology, vol. 11, No. 9, pp. 792-801 (1983).

"Cyclic Hematopoiesis in Dogs: Studies of Erythroid Burst-forming Cells Confirm an Early Stem Cell Defect"; Abkowitz, Janis, L., Holly, Richard D., Hammond, William P. IV, Experimental Hematology, 16:941-945 (1988).

"Hematopoietic Effects of Benzene Inhalation Assessed by Long-term Bone Marrow Culture"; Abraham, Nadar G., Enviromental Health Perspectives, vol. 104, Supplement 6, pp. 1277-1282 (1996).

"Circadian cell cycle variation of erythro- and myelopoiesis in humans"; Abrahamsen, JF, Smaaland, R, Sothern, RB, Laerum OD, European Journal of Haematology, vol. 58, pp. 333-345 (1997).

"Circadian and seasonal variations of hematopoiesis in cord blood"; Baudoux, E., et al, Bone Marrow Transplantation, Supplement 1, S12, p. 22 (1998).

"Toxicity on Human Hemopoietic Progenitors of 2'-2'-Difluoro-2'Deoxycytidine (Gemcitabine)"; Botta, Marco, et al, Anticancer Research, vol. 18, pp. 1037-1042 (1998).

"Measurement of the ADP:ATP ratio in human leukaemic cell lines can be used as an indicator of cell viability, necrosis and apoptosis"; Bradbury, D.A., Simmons, T.D., Slater, K.J., Crouch, S.P.M., Journal of Immunological Methods 240, pp. 79-92 (2000).

"The Growth Of Mouse Bone Marrow Cells In Vitro"; Bradley, T.R., Metcalf, D, Aust. J. Experimental Biological Medical Science, 44, pp. 287-300 (1966).

"Cyclic oscillations of neutrophils, monocytes, and CD8-positive lymphocytes in a healthy subject"; Carulli, Giovanni, et al, Haematologica, vol. 85(4), pp. 447-448 (2000).

"Azidothymidine and interferon-$\alpha$ in vitro effects on hemotopoiesis: Protective in vitro activity of IL-1 and GM-CSF"; Castello, G, et al, Experimental Hematology 23, pp. 1367-1371 (1995).

"Hematotoxicity of 5-Fluorouracil-Leucovorin in a Setting of Adjuvant Chemotherapy"; Cerruti, Allessandro, et al, Anticancer Research 14, pp. 2163-66 (1994).

"Chemopreventive Agent Resveratrol, a Natural Product Derived From Grapes, Triggers CD95 Signaling-Dependent Apoptosis in Human Tumor Cells"; Clement, M., et al, Blood, vol. 92, No. 3, pp. 996-1002 (1998).

"Idarubicinol myelotoxicity: a comparison of in vitro data with clinical outcome in patients treated with high-dose idarubicin"; Corsini, C., et al, British Journal of Cancer, 82(3), pp. 524-528 (2000).

"The use of ATP bioluminescence as a measure of cell proliferation and cytotoxicity"; Crouch, S.P.M., et al, Journal of Immunological Methods, 160, pp. 81-88 (1993).

"Experimental basis for increasing the therapeutic index of carboplatin in brain tumor therapy by pretreatment with WR compounds"; Dox, F., et al, Cancer Chemother Pharmacol, 28, pp. 308-310 (1991).

"Benzene-Induced Hematotoxicity and Bone Marrow Compensation in B6C371 Mice"; Farris, Georgia M., et al, Fundamental and Applied Toxicology 36, pp. 119-129 (1997).

"Hematotoxicity on human bone marrow- and unbilical coard blood-derived progenitor cells and in vitro therapeutic index of methoxymorpholinyldoxorubicin and its metabolites"; Ghielmini, M., et al, Cancer Chemother Pharmacol 42, pp. 235-240 (1998).

"In vitro schedule-dependency of myelotoxicity and cytotoxicity of Ecteinascidin 743 (ET-743)"; Ghielmini, M., et al, Annals of Oncology 9, pp. 989-993 (1998).

"Differential toxicity of anticancer drugs on late (GM-CFC) and early (LTC-IC) hemopoietic progenitors in vitro"; Ghielmini, M., et al, Cell Biology and Toxicology 15, pp. 395-404 (1999).

"Inhibition of CFU-E/BFU-E by 3'-Azido-3'-doexythymidine, Chlorpropamide, and Protoporphirin IX Zinc (II): A Comparison between Direct Exposure of Progenitor Cells and Long-Term Exposure of Bone Marrow Cultures"; Gribaldo, L., et al, Toxicological Sciences 58, pp. 96-101 (2000).

"Hemotopoietic dynamics in grey collies"; Haurie, Caroline, et al, Experimental Hematology 27, pp. 1139-1148 (1999).

"The Organization of Hemopoietic Tissue as Inferred from the Effects of 5-Fluorouracil"; Hodgson, G.S., Bradley, T.R. & Radley, J.M., Experimental Hematology, vol. 10, No. 1, pp. 26-35 (1982).

"In Vitro Production of CFU-S and Cells with Erythropoiesis Repopulating Ability by 5-Fluorouracil Treated Mouse Bone Marrow"; Hodgson, G.S., Bradley, T.R. & Radley, J.M., International Journal of Cell Cloning 1, pp. 49-56 (1983).

"Monoterpenes As Regulators Of Malignant Cell Proliferation"; Hohl, Raymond J., Adv. Exp. Med. Biol., vol. 401, pp. 136-146 (1996).

"The Myelotoxicity of chloramphenicol: in vitro and in vivo studies: I. In vitro effects on cells in culture"; Holt, D.E.,e t al, Hum. Exp. Toxicol., vol. 16, pp. 570-576 (1997).

"Colorimetric determination of inhibition of hematopoietic progenitor cells in solft agar"; Horowitz, D. & King, Andrew G., Journal of Immunlogical Methods 244, pp. 49-58 (2000).

"Erythroid Colony Formation in Cultures of Mouse and Human Bone Marrow: Analysis of the Requirement for Erythropoietin by Gel Filtration and Affinity Chromatography on Agarose-Concanavalin A"; Iscove, N., Sieber, F. & Winterhalter, H., Journal of Cell. Physiology, 83, pp. 309-320 (1974).

"A Miniaturized Agar Culture System for Cloning Human Erythropoietic Progenitor Cells"; Konwalinka, G., et al, Experimental Hematology, vol. 12, pp. 75-79 (1984).

"Use of the Microculture Kinetic Assay of Apoptosis to Determine Chemosensitivities of Leukemias"; Kravtsov, V.D., et al, Blood, vol. 92, No. 3, pp. 968-980 (1998).

"Chrono Biological Aspects Of Bone Marrow And Blood Cells"; Laerum, O.D. & Aardal, N.P., 11th Int'l Congress of Anatomy: Biological Rhythms in Structure and Function, pp. 87-97 (1981).

"Hematopoiesis occurs in rhythms"; Laerum, O.D., Experimental Hemotology 23, pp. 1145-1147 (1995).

"In Vitro Toxicity of A 3'-Azido-3'-Deoxythymidine and Hydroxyurea Combination on Normal Myeloid Progenitors"; Lerza, R., et al, Anticancer Research 18, pp. 2755-2758 (1998).

"Improved Plasma Culture System for Production of Erythrocytic Colonies In Vitro: Quantitative Assay Method for CFU-E"; McLeod, D.L., et al, Blood, vol. 44, No. 4, pp. 517-534 (1974).

"Rapid Colorimetric Assay for Cellular Growth and Survival: Application to Proliferation and Cytotoxicity Assays"; Mosman, Tim, Journal of Immunological Methods, vol. 65, pp. 55-63 (1983).

"A sensitive sandwich ELISA for measuring erythropoietin in human serum"; Noe, G., et al, British Journal of Haematology, vol. 80, pp. 285-292 (1992).

"Roles for In Vitro Myelotoxicity Tests in Preclinical Drug Development and Clinical Trial Planning"; Parchment, R.E., et al, Toxicologic Pathology, vol. 21, No. 2, pp. 241-250 (1993).

"Predicting hematological toxicity (myelosuppression) of cytotoxic drug therapy from in vitro tests"; Parchment, R.E., et al, Ann Oncol., vol. 9, pp. 357-364 (1998).

"In vitro Study of Pesticide Hematotoxicity in Human and Rat Progenitors"; Parent-Massin, D. & Thouvenot, D., Journal of Pharmacological and Toxicological Methods, vol. 30, pp. 203-207 (1993).

"Use of Limiting-Dilution Type Long-Term Marrow Cultures in Frequency Analysis of Marrow-Repopulating and Spleen Colony-forming Hematopoietic Stem Cells in the Mouse"; Ploemacher, R.E., et al, Blood, vol. 78, No. 10, pp. 2527-2533 (1991).

"The Induction of Clones of Normal Mast Cells By A Substance From Conditioned Medium"; Pluznik, D.H. & Sachs, L., Experimental Cell Research, vol. 43, pp. 553-563 (1966).

"The Effect of Stem Cell Proliferation Regulators Demonstrated With an in vitro Assay"; Pragnell, I.B., et al, Blood, vol. 72, No. 1, pp. 196-201 (1988).

"ECVAM's in-house prevalidation/validation studies in the areas of haematotoxicity, reproductive toxicity, metabolism-mediated toxicity and epithelial barrier function"; Prieto, Pilar, The Sciences of the Total Environment, vol. 247, pp. 349-354 (2000).

"The Effect of 5-Fluorouracil on Erythropoiesis"; Rich, Ivan, Blood, vol. 77, No. 6, pp. 1164-1170 (1991).

"The Developmental Biology of Hemopoiesis: Effect of Growth Factors on the Colony Formation by Embryonic Cells"; Rich, Ivan, Experimental Hematology, vol. 20, pp. 368-370 (1992).

"Specific Enhancement of Mouse CFU-E by Mouse Transferrin"; Rich, Ivan, et al, British Journal of Haematology, vol. 49, pp. 567-573 (1981).

"The effect of reduced oxygen tension on colony formation of erythropoietic cells in vitro"; Rich, Ivan, & Kubanek, B., British Journal of Haematology, vol. 52, pp. 579-588 (1982).

"Haemopoietic stem cells are organized for use on the basis of their generation-age"; Rosendaal, M., et al, Nature, vol. 264, pp. 68-69 (1976).

"Circadian Variation in Cell Division of the Mouse Alimentary Tract, Bone Marrow and Corneal Epithelium"; Scheving, L., et al, Anat. Rec., vol. 191, pp. 479-486 (1978).

"The Toxicology of Benzene"; Synder, Robert., et al, Environmental Health Perspectives, vol. 100, pp. 293-306 (1993).

"What controls hair follicle cycling?"; Stenn, K.S., et al, Experimental Dermatology, vol. 8, pp. 229-236 (1999).

"Distinct circadian time structures characterize myeloid and erythroid progenitor and multipotential cell clonogenicity as well as marrow precursor proliferation dynamics"; Wood, Patricia, et al, Experimental Hematology, vol. 26, pp. 523-533 (1998).

"Expression of the Circadian Clock genes *clock* and *period1* in Human Skin"; Zanello, Susana, et al, Journal of Invest Dermatol., vol. 115, pp. 757-760 (2000).

"The sensitivity of in vitro erythropoietic progenitor cells to different erythropoietin reagents during development and the role of cell death in culture"; Zimmerman, Frank & Rich, Ivan, Experimental Hematology, vol. 24, pp. 330-339 (1996).

Abstract: "Measurement of T-lymphocyte responses in whole-blood cultures using newly synthesized DNA and ATP" by Sottong, P.R., et al., *Clinical and Diagnostic Laboratory Immunology*, vol. 7, No. 2, pp. 307-311 (Mar. 2, 2000).

Abstract: "Bioluminescent assay for human lymphocyte blast transformation" by Bulanova, E.G., et al., *Immunology Letters*, vol. 46, No. 1-2, pp. 153-155 (1995).

"Replating potential of colony-forming units of granulocytes/macrophages (CFU-GM) expanded ex vivo by stem cell factor, interleukin (IL)-3, IL-6, granulocyte colony-stimulating factor, erythropoietin with or without thrombopoietin" by Katayama, Yoshio, et al., *International Journal of Hematology*, vol. 68, No. 2, pp. 157-168 (Aug. 1998).

"Rapid differentiation of a rare subset of adult human lin(-)CD34(-)CD38 (-) cells stimulated by multiple growth factors in vitro", by Fujisaki, T., et al., *Blood*, vol. 94, No. 6, pp. 1926-1932 (Sep. 15, 1999).

"Multi-level effects of flt3 ligand on human hematopoiesis: expansion of putative stem cells and proliferation of granulomonocytic progenitors/monocytic precursors", by Gabbianelli, M., et al., *Blood*, vol. 86, No. 5, pp. 1661-1670 (Sep. 1, 1995).

"C-mpl mutations are the cause of congenital amegakaryocytic thrombocytopenia" by Ballmaier, M., et al., *Blood*, vol. 97, No. 1, pp. 139-146 (2001).

"The Effects of Oxygen Tension on Haemopoietic and Fibroblast Cell Proliferation In Vitro" by Bradley, T.R., et al., *Journal of Cellular Physiology*, vol. 97, No. 3, pp. 517-522 (Dec. 1978).

* cited by examiner

HIGH-THROUGHPUT ASSAY OF HEMATOPOIETIC STEM AND PROGENITOR CELL PROLIFERATION

PRIORITY CLAIM

This application is a continuation-in-part of U.S. non-provisional application Ser. No. 10/059,521 filed Jan. 29, 2002 and also claims the benefit of the filing date of U.S. provisional application, Ser. No. 60/404,972, filed Aug. 21, 2002, the contents of which are also hereby incorporated by reference in their entireties.

This invention was made with government support under Small Business Innovation Research (SBIR) grant number 1R43CA93244-02 awarded by the NIH. The government has certain rights in the invention.

FIELD OF THE INVENTION

The present invention relates generally to high-throughput assay methods that determine the proliferative status of hematopoietic stem and progenitor cells. The present invention further relates to kits comprising reagents and instructions for the use thereof to perform the assays of the present invention

BACKGROUND

Two major concerns in drug development are the need to predict the efficacy and safety of a potential drug candidate before clinical trials are initiated, and how to predict which individual cancer cases are going to respond to a particular treatment. During the development process, therefore, drug candidates are typically batch tested on a variety of cell lines. Those that seem to have the desired effect on the cell lines are then tested in animals during the preclinical phase. Neither process, however, replicates the true clinical situation. As a result, patients in clinical trials often have to endure unpleasant and sometimes harmful effects because neither differential sensitivity nor patient variability was adequately considered during the drug developmental phases.

To overcome these deficiencies, in vitro cell-based assays that demonstrate a high degree of predictability during different phases of drug development are needed. In addition, there is a need for high throughput assays for screening large numbers of potential drug candidates produced during the discovery phase of drug development and allow those demonstrating promise to continue further in research and development. It therefore follows that assays based on primary cells exhibiting a high degree of predictability, coupled with a high-throughput component, could have a significant impact and value on the drug development process.

The hematopoietic system is one of five continuously proliferating systems of the body, the others being the epithelial mucosa of the gastrointestinal tract, the dermis of the skin, the germ cells of the reproductive organs and the epithelium of the eye cornea. All five proliferating systems share common characteristics, the most important being that a small population of stem cells maintains the continuous production of mature end cells. They all possess the same structural organization of four basic compartments, namely the stem cell, amplification and differentiation, maturation and mature cell compartments.

The hematopoietic system, however, is unique in several ways. It is the only system capable of producing at least eight functionally different cell lineages from a single pluripotent stem cell. Assays are available that allow the differential effect of drugs on the various lympho-hematopoietic lineages to be examined. Second, the site of cell production changes during ontological development. This helps in differential sensitivity testing. Third, the site of production in the adult is the bone marrow, which is a significantly different tissue from the functional site of the peripheral circulation. Fourth, compared with other proliferating systems, and almost all other systems of the body, adult hematopoietic stem and progenitor cells are readily accessible.

Hematopoietic stem and progenator cell lineages can be used to measure parameters that would normally be inaccessible. For example, peripheral blood contains mature end cells that can be readily obtained to measure red and white blood cell counts, differential counts and other end stage blood parameters. These parameters are conventionally used in preclinical drug testing and form the basis of the National Cancer Institute (NCI) guidelines for hemotoxicity testing during clinical trials. However, these parameters have little if any predictive value as to, for example, the cytotoxic effect of therapeutic compounds on primitive hematopoietic cells or the stem cells of other proliferating tissues.

Besides the mature red and white blood cells, the peripheral blood also contains circulating populations of stem and progenitor cells that can be isolated and used for hematopoietic status monitoring and hemotoxicity testing. The so-called granulocyte-macrophage colony-forming cell (GM-CFC) assay and the enumeration of $CD34^+$ cells (stem and early progenitor cells) currently form the basis of quality control for hematopoietic stem cell transplantation.

The widespread use of in vitro hematopoietic assays was initiated when soluble factors released by fibroblasts were shown to be capable of stimulating cells to form granulocyte-macrophage colonies in soft agar (Bradley & Metcalf, *Aust. J. Exp. Biol. Med* 44, 287-287 (1987); Pluznik & Sachs, *Exp. Cell Res.* 43, 553-553 (1966)). Colony forming assays (CFAs) for erythropoietic progenitor cells (McLeod et al., *Blood* 44, 617-534 (1974); Iscove et al., *J Cell Phyisol.* 2-23 (1974); Axelrad et al., *Haemopiesis in Culture* 226-223 (1974)) and other hematopoietic lineages were also developed. The use of cytotoxic drugs such as 5-fluorouracil (Hodgson et al., *Exp. Hemat.* 10, 26-36 (1982) and *Int. J. Cell* Cloning 1, 49-56 (1983)) and hydroxyurea (Rosendaal et al., Nature 264, 68-69 (1976)) allowed the hierarchy within the stem cell compartment to be elucidated and in vitro assays for primitive stem cell populations to be developed (Ploemacher et al., *Blood* 78, 2527-2536 (1991); Sutherland et al., *Blood* 72, 104a (1988)).

In vivo, an insult at the stem or early progenitor cell level requires a certain amount of time for the effect to be detected at the peripheral blood level. The effect may not be observed for weeks, or even months. This does not provide a high level of predictability and is why end stage cell parameters cannot be used to predict the effect of an agent. By the time the effect is observed, adverse reactions by the patient have already occurred.

In vitro colony-forming assays based on stem or progenitor cells, on the other hand, can fulfill the requirements of prediction and sensitivity because they detect the effect of the insult before it is observed in the circulation. Colony-forming assays for leukemic cells are also available. In these classic assays, the more primitive the cell to be detected, the longer it takes to detect its progeny in the form of a colony. The proliferative potential of the cells being analyzed, and their ability to be stimulated by growth factors in vitro are essential for these assays. This dependency on the amplification compartment inherent in the hematopoietic system is often overlooked and without this component colony-forming assays in general, and especially predictive hemotoxicity testing, could not be performed.

Under steady-state conditions, the proliferative status of primitive stem cells is considered to be quiescent, while the proportion of cells in cell cycle increases with stem cell maturity. Once the stem cell has become determined with respect to a cell lineage, it enters the amplification compartment for producing the large and constant number of mature cells. With entry into the cell cycle, however, the cell becomes vulnerable to exogenous agents including the cytotoxic drugs typically used in oncology. Thus, the GM-CFC assay, for example, has been used to predict myelosuppression (Prieto, P., *Sci. Total Environ.* 247, 349-354 (2000)). The predictive quality of this assay, has been proven by validation studies with alkylating agents (Parchment et al., *Toxicol. Pathol.* 21, 241-250 (1993)). Additionally, however, if the maximum tolerated drug concentration for hematopoietic cells can be predicted, hemotoxicity studies would play an important role in drug discovery since it would be a toxic/therapeutic index-based assay (Parchment et al., *Ann. Oncol.* 9, 357-364 (1998)).

In the case of cytotoxic drug testing, the target cells have to be in cell cycle. For any drug that relies on cell proliferation, the tissues most affected or damaged by toxicity are those actively engaged in cell proliferation, which includes the bone marrow and the gastrointestinal tract. It therefore follows that hemotoxicity testing could also usefully be extrapolated to, and predictive for, the effects of a potential drug on other proliferating tissues.

Toxicity in general, and hemotoxicity in particular, can also be correlated with the time of drug administration. The therapeutic index of a drug, and hence its toxicity, is dependent, in part on the circadian variation in the hematopoietic cell division of rodents (Laerum, O. D., *Exp. Hematol.* 23, 1145-1147 (1995); Aardal et al., *Exp. Hemtol.*, 11, 792-801 (1993); Aardal, *Exp. Hematol.* 12, 61-67 (1984); Wood et al., *Exp. Hematol.*, 26, 523-533 (1998)), dogs (Haurie et al., *Exp. Hematol.* 27, 1139-1148 (1999); Abkowitz et al., *Exp. Hematol.* 16, 941-945 (1988)) and in humans (Abrahamsen et al., *Eur. J. Haematol.* 58, 333-345 (1997); Baudoux et al., *Bone Marrow Transplant* 22 (Suppl. 1) S 12 (1998); Carulli et al., *Hematologica* 85, 447-448 (2000)). Similarly, cells of the gut mucosa (Schering et al., *Anat. Rec.* 191, 479-486 (1978)), Sterm & Paus, *Exp. Dermatol.* 8, 229-233 (1999); Zanello et al., *J. Invest. Dermatol.* 115, 757-760 (2000)) and the corneal epithelium of the eye (Schening et al., *Anat. Rec.* 191, 479-486 (1978)) exhibit circadian organization. For human bone marrow and gastrointestinal tissues, for example, S-phase DNA synthesis preferentially occurs in the morning hours rather than in the evening or nighttime hours. This implies cytotoxic agents might be less toxic and exhibit high efficacy if given at a time when the proliferative status of the cells is at a nadir in these tissues.

For toxicity testing, large numbers of comparative samples are needed, thereby making the enumeration of manual CFAs for this purpose impractical. CFAs also suffer from a lack of standardized colony enumeration procedures, and the subjectivity and high degree of expertise of the personnel and the time required for accurate enumeration of the colonies. The long culture periods required to visualize the proliferative potential of different cell populations is also a disadvantage. However, the culture period is an inherent property of the cell population and cannot be changed.

Conventional cell proliferation assays have measured either $^3$H-thymidine or 5-bromo-deoxyuridine (BrdU) incorporation. The BrdU assay can use microscopy, flow cytometry or absorbance. Colorimetric tetrazolium compounds, in particular 3-[4,5-dimethylthiazol-2yl]-2,5-diphenyltetrazolium bromide (MTT), (Mosmann, *J. Immunol. Meth.* 65, 666 (1983)), have also been used. Horowitz and King, *J. Immunol. Meth.* 244, 49-58 (2000)) developed a multi-well, murine colony-forming assay in soft agar whereby the enumeration of cell proliferation or inhibition was measured using the MTT colorimetric method. Results were equivalent to the colony-forming assay. The number of target cells was reduced to $1.25 \times 10^4$ cells/ml, but only studied granulocyte/macrophage progenitor cells were tested and not stem cells, erythropoietic or megakaryopoietic progenitor cells. However, it is also desirable to have an assay system that can accommodate the complete range of target cell populations that can be cultured and subjected to drug-induced hemotoxicity effects.

Hematological malignancies rank 5th and 6th in the cause of deaths for men and women respectively and use of stem cell transplants using peripheral blood, bone marrow and umbilical cord blood have increased dramatically. Reconstitution of the patient after a transplant, however, usually occurs in about 14 days, which is the same time required for the conventional, manual, CFA to detect the growth potential of transplanted cells. Therefore, the usefulness of the GM-CFC assay as an indicator and quality control measure for the growth potential of the transplantable cells is limited. Reliance is often placed on measuring the number of CD34+ cells by flow cytometery, even though this provides no information as to the cell growth potential. Therefore, there is a need for a sensitive, rapid and cost-effective assay that can be used as an indicator for hematopoietic engraftment and reconstitution potential. The patient would benefit significantly because, if engraftment and reconstitution of the lympho-hematopoietic system does not occur after transplantation, the physician can rapidly detect this rejection and proceed with a second transplant, offering reduced financial implications in lower hospitalization and medication costs and improved patient comfort and recovery.

These and other objectives and advantages of the invention will become fully apparent from the description and claims that follow or may be learned by the practice of the invention.

SUMMARY OF THE INVENTION

Briefly described, the present invention relates generally to kits that provide reagent mixes and instructions for the use thereof, in performing high-throughput assay methods that determine the proliferative status of isolated target cell populations. The methods measure the luminescent output derived from the intracellular ATP content of incubated target cells, and correlate the luminescence with the proliferative status of the cells. The present invention further relates to kits that provide reagent mixes and instructions for the use thereof in high-throughput assays methods for screening compounds that may modulate the proliferative status of a target cell population. The kits of the present invention and methods therein described may be used for determining the proliferative status of any isolated cell line or type. The kits and methods of the present invention address the need for rapid assays that will determine the proliferative status of isolated hematopoietic stem and progenitor cells and of subpopulations of differentiated cells thereof.

One aspect of the present invention provides kits and instructions for the use of the kits in a high-throughput assay method useful for rapidly determining the proliferative status of a population of cells, such as primitive hematopoietic cells, as a function of the ATP content of the cells, the method comprising incubating a target cell population in a cell growth medium having a concentration of fetal bovine serum of between 0% and about 30%, a concentration of methyl cellulose between about 0.4% and about 0.7%, and in an atmosphere having less than about 7.5% oxygen. The cell population is then contacted with a reagent capable of generating luminescence in the presence of ATP. The level of luminescence correlates with the amount of ATP in the cell population, wherein the amount of ATP indicates the proliferative status of the target cell population.

The method of the present invention may further comprises contacting the target cell population with at least one cytokine and may further comprise generating a cell population enriched in hematopoietic stem cells, or a hematopoietic progenitor cell lineage.

The kits and instructions of the present invention are also suitable for a high-throughput assay method for rapidly identifying a compound capable of modulating the proliferative status of a target cell population. In this aspect of the present invention, a first target cell population is incubated in cell growth medium comprising a concentration of fetal bovine serum between 0% and about 30%, a concentration of methyl cellulose between about 0.4% and about 0.7%, and in an atmosphere having less than about 7.5% oxygen and, typically, a cytokine. The method further comprises providing a first and a second target cell population, and contacting the first and second target cell populations with at least one test compound, contacting the target cell populations with a reagent capable of generating luminescence in the presence of ATP. The luminescence generated is detected by the reagent contacting the target cell populations, the level of luminescence indicating the proliferative status of the target cell population. The proliferative status of the first target cell populations is compared with the proliferative status of the second target cell population, thereby identifying a test compound capable of modulating the proliferative status of a target cell population.

Another aspect of the present invention is kits that comprise a plurality of vessels, each vessel containing one or more of the reagents that, when combined, provide rapid and error-reduced methods for performing the Hematopoietic and/or Hematotoxicity Assays via Luminescence Output (HALO) procedures of the present invention Additional objects and aspects of the present invention will become more apparent upon review of the detailed description set forth below when taken in conjunction with the accompanying figures, which are briefly described as follows.

BRIEF DESCRIPTION OF THE FIGURES

FIGS. 1A-4B illustrate the correlation between the initial plated cell concentration (0.25, 0.5, 0.75, 1, 1.5 $2 \times 10^5$/well) and the mean (FIGS. 1A, 2A, 3A and 4A respectively) or sum (FIGS. 1B, 2B, 3B, and 4B respectively) of relative luminescence units (RLU) measured at 4 days (FIGS. 1A and 1B), 7 days (FIGS. 2A and 2B), 10 days (FIGS. 3A and 3B) and 14 days (FIGS. 4A and 4B) after culture initiation, as a function of the integration time and/or gain of the plate reader. In FIGS. 1A-4B the value 2000 represents an integration time of 2000 ms. "Max" represents the maximum integration time. The values 200, 215, 225 or 250 represent the gains that were used with the respective integration times.

DETAILED DESCRIPTION OF THE INVENTION

Figure 1:
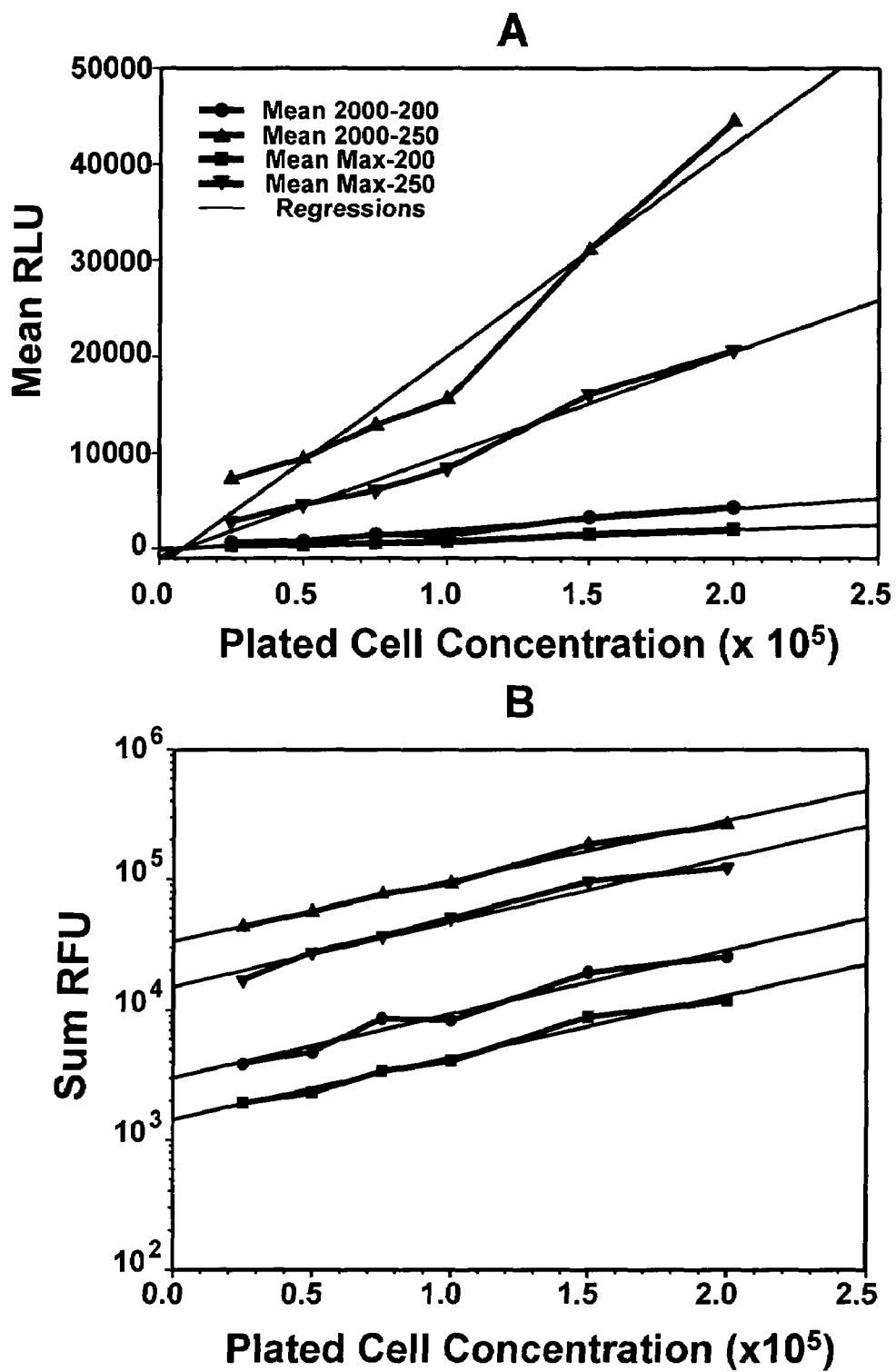
Figure 2:
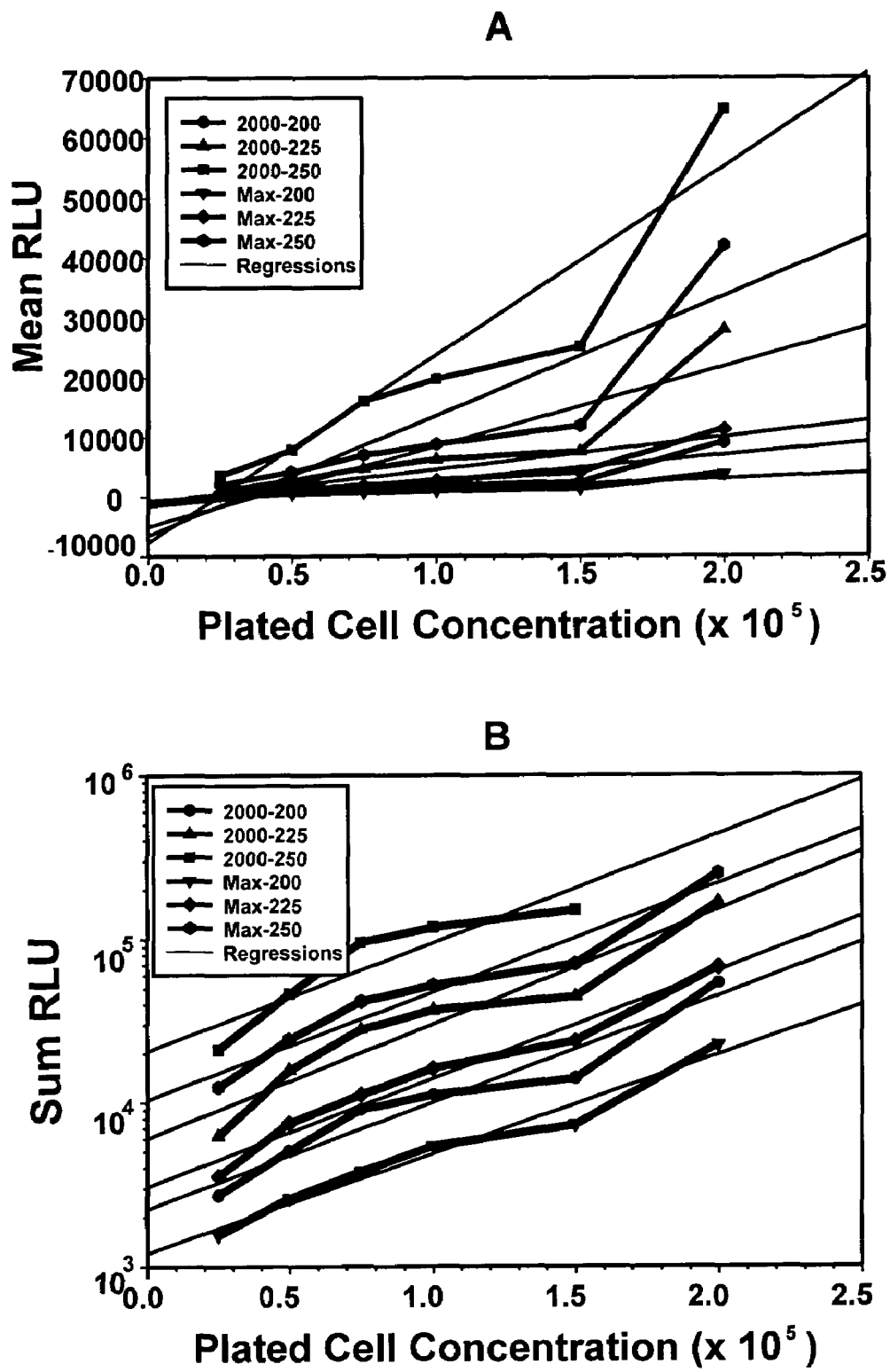
Figure 3:
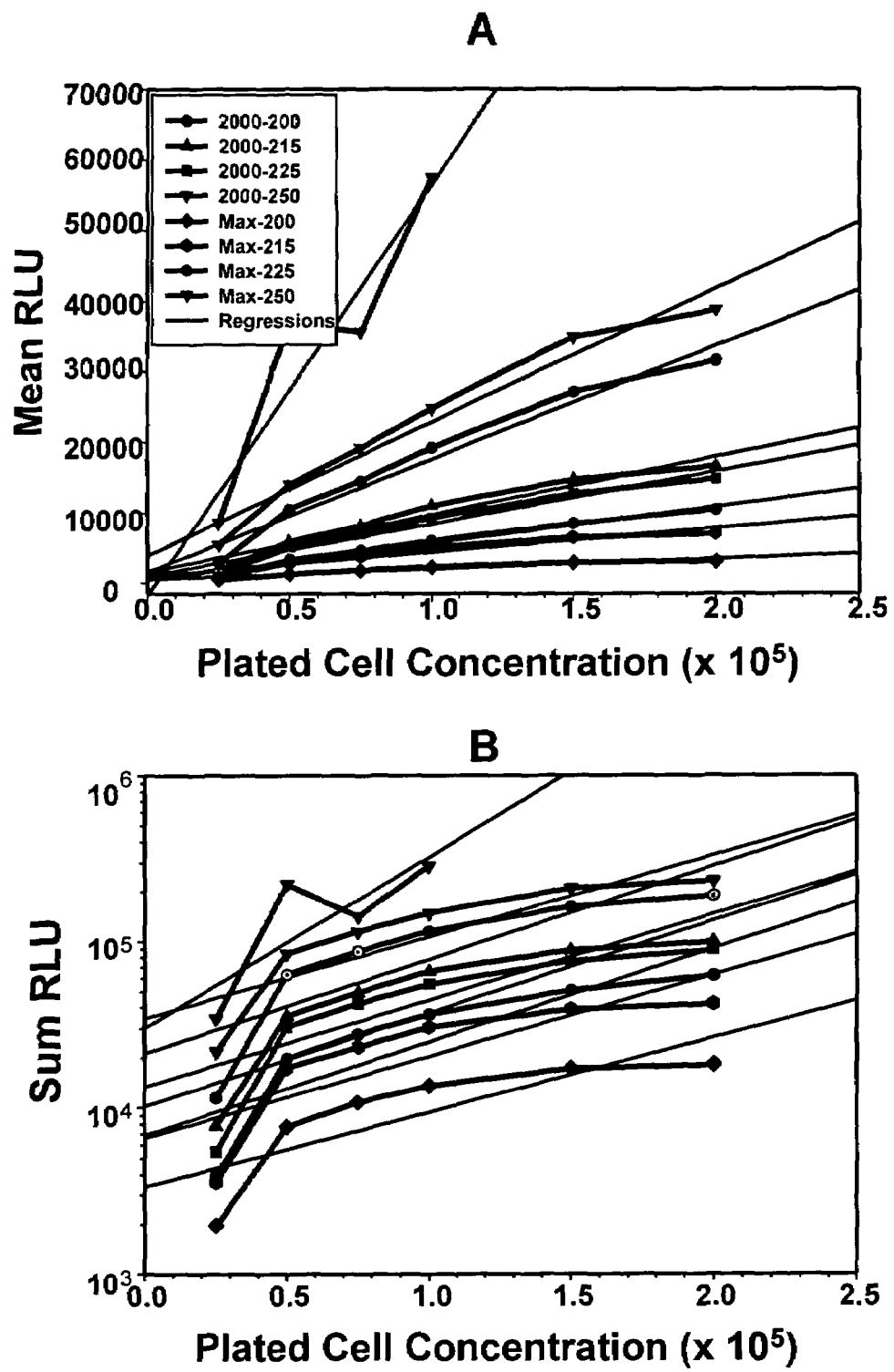
Figure 4:
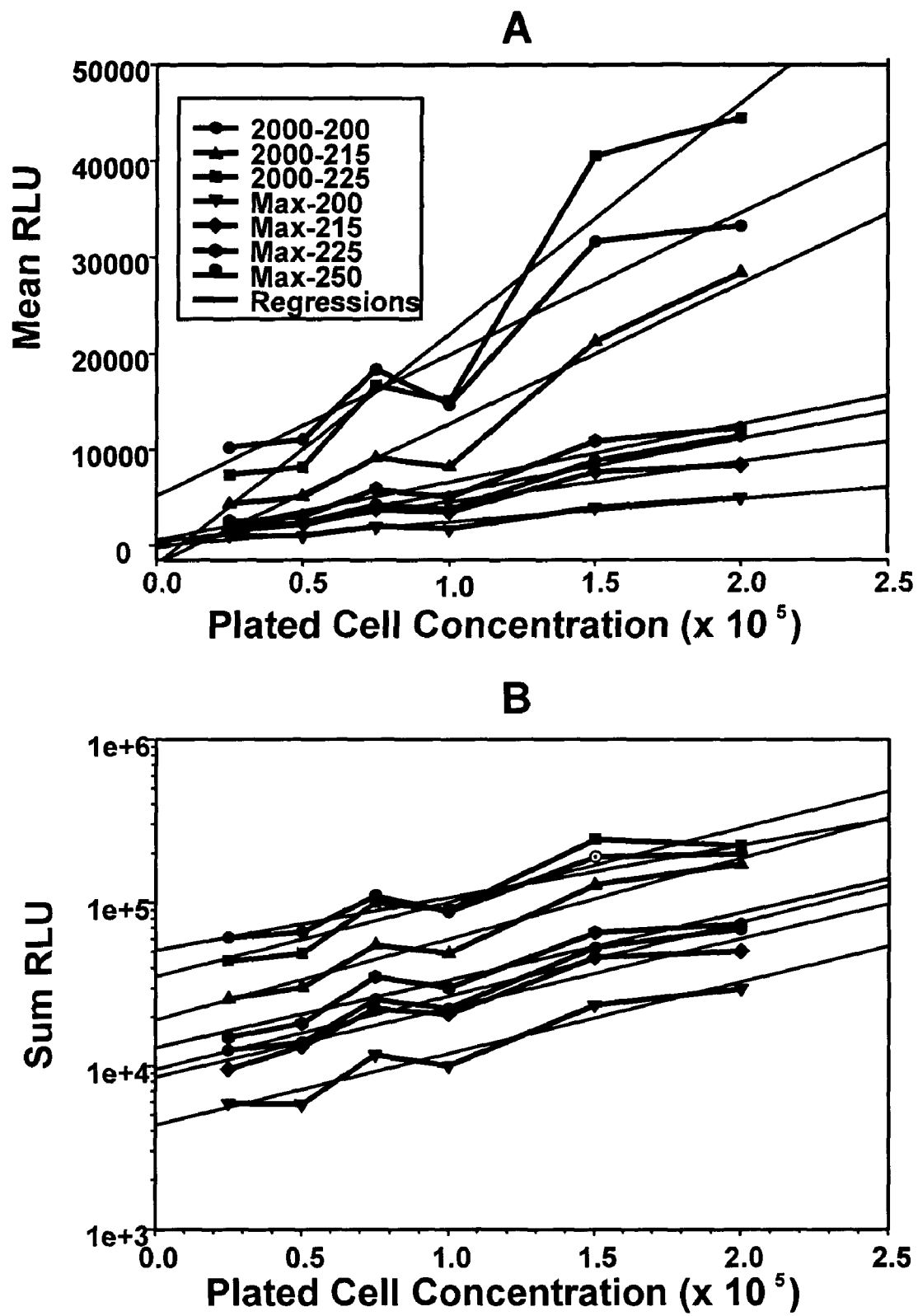

A full and enabling disclosure of the present invention, including the best mode known to the inventor of carrying out the invention, is set forth more particularly in the remainder of the specification, including reference to the Examples. This description is made for the purpose of illustrating the general principles of the invention and should not be taken in the limiting sense.

The present invention provides kits that comprise vessels, each vessel containing one or more of the necessary reagents mixes and instructions for the use thereof for performing the high-throughput assays of the present invention. The kits and instructions of the present invention provide high-throughput assays for detecting and measuring the proliferative status of populations of cells, especially of primitive hematopoietic stem and progenitor cells, and cell lineages derived therefrom.

The methods of the present invention are especially useful when applied to populations of primitive hematopoietic cells including primary cells isolated from peripheral blood cells and bone marrow cells and hematopoietic stem and progenitor cells. The methods of the present invention, however, may be applied to any population of proliferating cells, including cells isolated from tissues and solid tumors.

The methods of the present invention can also be used to distinguish subpopulations of cells that may differ in the response to cytotoxic inhibitors, or activators such as cytokines The methods may be used to optimize the inhibitors to achieve maximum efficacy against a subpopulation of proliferating cells. An optimized dose, determined from an isolated small sample of the cell population of a patient, may be administered to the proliferating cells in vivo, wherein the optimized dose may be administered systemically to the human or animal patient having the proliferating subpopulation of cells, thereby reducing the likelihood of potentially harmful side-effects to the recipient patient.

The high-throughput assay methods of the present invention may also be used to determine the proliferative status of a population of hematopoietic stem or progenitor cells to determine their suitability and acceptability for transplantation into a recipient animal or human patient.

Definitions

The term "animal" as used herein refers to any vertebrate animal other than a human having a population of cells wherein at least one subpopulation of the cells may be proliferating or induced to proliferate. The term "animal" as used herein also refers to mammals including, but not limited to, bovine, ovine, porcine, equine, canine, feline species, non-human primates including apes and monkies, rodents such as rat and mouse, and lagomorphs such as rabbit and hare.

The term "tissue" as used herein refers to a group or collection of similar cells and their intercellular matrix that act together in the performance of a particular function. The primary tissues are epithelial, connective (including blood), skeletal, muscular, glandular and nervous.

The term "cell" or "cells" as used herein refers to any cell population of a solid or non-solid tissue including, but not limited to, a peripheral blood cell population, bone marrow cell population, a leukemic cell line population and a primary leukemic cell line population or a blood stem cell population. The cells may be hematopoietic cells, including bone marrow, umbilical cord blood, fetal liver cells, yolk sac and differentiating embryonic stem cells or differentiating primordial germ cells or embryonic germ cells. The cells may be a primary cell line population including, but not limited to, a leukemic cell line. Examples of leukemic cell lines include, but are not limited to, an acute lymphocytic leukemia, an acute myeloid leukemia, a chronic lymphocytic leukemia, a chronic myeloid leukemia and a pre-B acute lymphocytic leukemia. Such cell lines include, but are not limited to, acute myelogenous leukemia, acute T-cell leukemia, acute lymphoblastic leukemia, chronic myeloid leukemia, acute monocytic leukemia and B-cell leukemia. The term "target cell population" as used herein refers to any cell population, especially hematopoietic stem and progenitor cells, or subpopulations thereof, that may be contacted with a test compound, wherein the test compound may modulate the proliferation of the cells in a positive or a negative direction depending upon the compound and the target cell population.

The term "cell line" refers to cells that are harvested from a human or animal adult or fetal tissue, including blood and cultured in vitro, including primary cell lines, finite cell lines, continuous cell lines, and transformed cell lines.

The term "cell lineage" as used herein refers to a cell line derived from a stem cell or progenitor cell that is committed to producing a specific functional cell including, but not limited to, mature cells of the a hematopoietic system.

The term "cell cycle" as used herein refers to the cycle of stages in the replication of a eukaryotic cell. The cycle comprises the four stages G1, S, G2 and M, wherein the S phase is that portion of the cycle wherein the nucleic acid of the cell is replicated. Thus, a cell identified as being in the S-phase of the cell cycle is also identified as being a proliferating cell.

The term "proliferative status" as used herein refers to whether a population of hematopoietic stem or progenitor cells, or a subpopulation thereof, are dividing and thereby increasing in number, in the quiescent state, or whether the cells are not proliferating, dying or undergoing apoptosis.

The terms "modulating the proliferative status" or "modulating the proliferation" as used herein refers to the ability of a compound to alter the proliferation rate of a population of hematopoietic stem or progenitor cells A compound may be toxic, wherein the proliferation of the cells is slowed or halted, or the proliferation may be enhanced such as, for example, by the addition to the cells of a cytokine or growth factor.

The term "quiescent" refers to cells that are not actively proliferating by means of the mitotic cell cycle. Quiescent cells (which include cells in which quiescence has been induced as well as those cells which are naturally quiescent, such as certain fully differentiated cells) are generally regarded as not being in any of the four phases G1, S, G2 and M of the cell cycle; they are usually described as being in a G0 state, so as to indicate that they would not normally progress through the cycle. Cultured cells can be induced to enter the quiescent state by various methods including chemical treatments, nutrient deprivation, growth inhibition or manipulation of gene expression, and induced to exit therefrom by contacting the cells with cytokines or growth factors.

The term "primary cell" refers to cells obtained directly from a human or animal adult or fetal tissue, including blood. The "primary cells" or "cell lines" may also be derived from a solid tumor or tissue, that may or may not include a hematopoietic cell population, and can be suspended in a support medium. The primary cells may comprise a primary cell line.

The term "primitive hematopoietic cell" as used herein refers to any stem, progenitor or precursor cell that may proliferate to form a population of hematopoietic cells.

The term "hematopoietic stem cells" as used herein refers to pluripotent stem cells or lymphoid or myeloid (derived from bone marrow) stem cells that, upon exposure to an appropriate cytokine or plurality of cytokines, may either differentiate into a progenitor cell of a lymphoid or myeloid cell lineage or proliferate as a stem cell population without further differentiation having been initiated. "Hematopoietic stem cells" include, but are not limited to, colony-forming cell-blast (CFC-blast), high proliferative potential colony forming cell (HPP-CFC) and colony-forming unit-granulocyte, erythroid, macrophage, megakaryocyte (CFU-GEMM) cells.

The terms "progenitor" and "progenitor cell" as used herein refer to primitive hematopoietic cells that have differentiated to a developmental stage that, when the cells are further exposed to a cytokine or a group of cytokines, will differentiate further to a hematopoietic cell lineage. "Progenitors" and "progenitor cells" as used herein also include "precursor" cells that are derived from some types of progenitor cells and are the immediate precursor cells of some mature differentiated hematopoietic cells. The terms "progenitor", and "progenitor cell" as used herein include, but are not limited to, granulocyte-macrophage colony-forming cell (GM-CFC), megakaryocyte colony-forming cell (Mk-CFC), burst-forming unit erythroid (BFU-E), B cell colony-forming cell (B-CFC) and T cell colony-forming cell (T-CFC). Precursor cells" include, but are not limited to, colony-forming unit-erythroid (CFU-E), granulocyte colony forming cell (G-CFC), colony-forming cell-basophil (CFC-Bas), colony-forming cell-eosinophil (CFC-Eo) and macrophage colony-forming cell (M-CFC) cells.

The term "cytokine" as used herein refers to any cytokine or growth factor that can induce the differentiation of a hematopoietic stem cell to a hematopoietic progenitor or precursor cell and/or induce the proliferation thereof. Suitable cytokines for use in the present invention include, but are not limited to, erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor, insulin-like growth factor, and insulin. The term "cytokine" as used herein further refers to any natural cytokine or growth factor as isolated from an animal or human tissue, and any fragment or derivative thereof that retains biological activity of the original parent cytokine. The cytokine or growth factor may further be a recombinant cytokine or a growth factor such as, for example, recombinant insulin. The term "cytokine" as used herein further includes species-specific cytokines that while belonging to a structurally and functionally related group of cytokines, will have biological activity restricted to one animal species or group of taxonomically related species, or have reduced biological effect in other species.

The terms "cell surface antigen" and "cell surface marker" as used herein may be any antigenic structure on the surface of a cell. The cell surface antigen may be, but is not limited to, a tumor associated antigen, a growth factor receptor, a viral-encoded surface-expressed antigen, an antigen encoded by an oncogene product, a surface epitope, a membrane protein which mediates a classical or a typical multi-drug resistance, an antigen which mediates a tumorigenic phenotype, an antigen which mediates a metastatic phenotype, an antigen which suppresses a tumorigenic phenotype, an antigen which suppresses a metastatic phenotype, an antigen which is recognized by a specific immunological effector cell such as a T-cell, and an antigen that is recognized by a non-specific immunological effector cell such as a macrophage cell or a natural killer cell. Examples of "cell surface antigens" within the scope of the present invention include, but are not limited to, CD3, CD4, CD8, CD34, CD90 (Thy-1) antigen, CD117, CD38, CD56, CD61, CD41, glycophorin A and HLA-DR, CD133 defining a subset of $CD34^+$ cells, CD19, and HLA-DR. Cell surface molecules may also include carbohydrates, proteins, lipoproteins or any other molecules or combinations thereof, that may be detected by selectively binding to a ligand or labeled molecule and by methods such as, but not limited to, flow cytometry.

The term "cell surface indicator" as used herein refers to a compound or a plurality of compounds that will bind to a cell surface antigen directly or indirectly, and thereby selectively indicate the presence of the cell surface antigen. Suitable "cell surface indicators" include, but are not limited to, cell surface antigen-specific monoclonal or polyclonal antibodies, or derivatives or combinations thereof, and which may be directly or indirectly linked to a signaling moiety. The "cell surface indicator" may be a ligand that can bind to the cell surface antigen, wherein the ligand may be a protein, peptide, carbohydrate, lipid or nucleic acid that is directly or indirectly linked to a signaling moiety.

The term "flow cytometer" as used herein refers to any device that will irradiate a particle suspended in a fluid medium with light at a first wavelength, and is capable of detecting a light at the same or a different wavelength, wherein the detected light indicates the presence of a cell or an indicator thereon. The "flow cytometer" may be coupled to a cell sorter that is capable of isolating the particle or cell from other particles or cells not emitting the second light.

The term "reagent capable of generating luminescence in the presence of ATP" as used herein refers to a single reagent or combination of components that, in the presence of ATP, will generate luminescence. The amount of luminescence may be reliably related to the amount of ATP present. An example of a reagent suitable for use in the present invention is the combination of luciferin and luciferase as described by Crouch et al. (*J. Immunol. Meth.* 160, 81-88 (2000)) and Bradbury et al. (*J. Immunol. Meth.* 240, 79-92 (2000) incorporated herein by reference in their entireties.

The term "toxicity" as used herein refers to the ability of a compound or a combination of compounds to negatively modulate the proliferation of a population of hematopoietic stem or progenitor cells. It will be understood that the toxicity of a compound or compounds may be effective against one hematopoietic cell lineage and not against another, and may further include the ability of a compound to modulate the differentiation of a hematopoietic stem or progenitor cell.

The term "differentially distinguishable" as used herein refers to hematopoietic stem and progenitor cells, or any other animal cell, the proliferation status of which may be usefully determined by the assay methods of the present invention and which can be characterized into subpopulations based on, for example, different complements of cell surface markers.

Following longstanding law convention, the terms "a" and "an" as used herein, including the claims, are understood to mean "one" or "more".

Abbreviations

Abbreviations used in the present specification include the following: HALO, Hematopoietic and/or Hematotoxicity Assays via Luminescence Output; IL, interleukin; PBMC, peripheral blood mononuclear cells; PBS, phosphate-buffered saline (10 mM phosphate, 138 mM NaCl, 2.7 mM KCl, pH 7.4); FBS, fetal bovine serum; BSA, bovine serum albumen; BITSI, (B)ovine serum albumin, recombinant human (I)nsulin, iron-saturated (T)ransferrin, (S)erum and (I)MDM; IMDM, Iscove's modified Dulbecco's medium.

Reference now will be made in detail to the aspects and embodiments of the invention. Each example is provided by way of explanation of the invention, and not a limitation of the invention. In fact, it will be apparent to those skilled in the art that various modifications, combination, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

The high-throughput assay methods of the present invention comprise determining the proliferative status of a target cell population by measuring the metabolic activity of samples of proliferating cells as indicated by their ATP content. The ATP content can be measured by detecting the luminescence generated by a ATP-dependent reaction requiring, for example, by contacting the cells with an ATP-releasing agent and an ATP luminescence-monitoring agent. A suitable system for detecting ATP by the emission of luminescence comprises the combination of luciferin and luciferase, although it is contemplated that any method that will emit a detectable signal, the intensity of which may be correlated to the amount of ATP in a cell culture may be within the scope of the present invention.

The high-throughput assay (HALO) method of the present invention allows for the detection of actively proliferating target cell populations, especially, but not limited to, hematopoietic stem and progenitor cell lineages that have been induced to undergo proliferation by exposure of the cell population to one or more cytokines. Most hematopoietic cell lineages can be induced to proliferate by contacting the cell population with at least one appropriate cytokine. It is, therefore, contemplated that a cytokine, or combination of cytokines, may be selected to induce the proliferation of a selected cell lineage. It is further contemplated to be within the scope of the assay methods of the present invention for a plurality of primitive hematopoietic stem or progenitor cell populations to be contacted with a plurality of cytokines or combinations of cytokines, thereby establishing populations of different proliferating cell lineages. The various proliferating cell lineages may then be used as target cells and contacted with one or more test compounds. The cell proliferation modulating activities, including toxicity, of the compounds or combinations and/or doses thereof may be compared and contrasted, as well as how the various cell lineages will react to the test compounds. The present invention provides kits comprising a vessel or vessels that contain reagent mixes required for the HALO method, and instructions for performing this method.

High-throughput Assays of Hematopoietic Stem and Progenitor Cell Proliferation (Hematopoietic and Hematotoxicity Assays via Luminescence Output (HALO))

The HALO platform of the present invention provides the biotechnology and pharmaceutical industry with a rapid, high-throughput, multifunctional testing system that can be used at all stages of drug development from screening to clinical trials. HALO is a proliferation assay with a luminescence readout typically performed in a 96-well plate. The present invention provides kits that can allow up to 11 different stem, progenitor and precursor cell populations, from different hematopoietic tissues, from at least five different species, to be detected and quantitatively measured simultaneously.

Primitive hematopoietic cells can be isolated from suitable animal or human tissues including, for example, peripheral blood, bone marrow, or umbilical cord blood. Mononuclear cells, for example peripheral blood mononuclear cells (PBMCs) may be further isolated by methods such as density-gradient centrifugation. It is contemplated to be within the scope of the present invention for the primitive cell population to be further subdivided into isolated subpopulations of cells that are characterized by specific cell surface markers. The methods of the present invention may further include the separation of cell subpopulations by methods such as high-speed high-speed cell sorting, typically coupled with flow cytometry.

For example, the channels of a flow-cytometer and high-speed cell sorter could be set at 530 nm, typically used for FITC labeling, 670 nm used for APC labeling, and a UV channel, for Hoechst (Ho) 33342 or DAPI staining. Fluorescent compensation software such as the System II or Expo 32 (Beckman Coulter) can allow full use of all of these channels. Cell subpopulations can be selected based on the presence or absence of cell membrane antigen markers, the intracellular pH, and the cell cycle status. Exemplary methods for selectively distinguishing subpopulations of hematopoietic cells are described, for example, in PCT application Serial No: 20010012620, incorporated herein in by reference in its entirety.

Multiparameter analysis may be conducted on primary normal and leukemic samples or leukemic cell lines. The methods of the present invention, however, may be applied or adapted to any non-leukemic hematopoietic stem or progenitor cell population that might include a subpopulation of proliferating cells. An antigen indicator conjugated to APC can be used to selectively detect a normal blood stem cell subpopulation. Aliquots of cells may be labeled with panels comprising more than one biomarker. An example of one such panel incorporates CD38-FITC, CD34-APC, SNARF and Ho33342. Other examples of possible panels can include substituting CD38-FITC with CD117(c-kit)-FITC, with CD91 (Thy-1)-FITC or with CD133-FITC.

The procedures of the present invention, therefore, can provide techniques to analyze combinations of cell markers as described above, or those specific for other lymphohematopoietic lineages to differentiate the effects of inhibitors on normal different cell subpopulations. A similar reasoning can be applied to leukemic cell populations that also show aberrant flow cytometric profiles distinguishable from the normal population. A typical example would be chronic myeloid leukemia in chronic phase. However, in the case of ALL, the leukemic cell population can be defined by a high proportion of $CD19^+$ cells. Therefore, CD19 is a biomarker that can be used to differentiate between leukemic and non-leukemic populations. The selected cell subpopulations can then be applied to the high-throughput assays of the present invention described in Examples 1 and 2 below.

Cell surface indicators may be contacted with the hematopoietic stem or progenitor cells or leukemic cells thereof and the various subpopulations may be selectively separated by techniques such as flow cytometry or by attaching the cell surface indicators directly or indirectly to a separable solid support such as magnetic beads. The beads and the attached cells thereon can be isolated by a magnetic field.

High-throughput Assay Methods for Toxicity Testing With Hematopoietic Stem and Progenitor Cells A cell lineage that is induced to proliferate by contacting a first primitive hematopoietic stem or progenitor cell population with a cytokine or combination of cytokines may further be contacted with a test compound that may have a cytotoxic effect or a cell proliferation enhancing effect. The degree of modulation of cell proliferation or differentiation may also be determined by comparing the proliferation of the cell lineage in the presence of the test compound, and in its absence from the culture of a second targeted cell population or plurality of second cell populations. It is within the scope of the assay methods of the present invention for a plurality of test compounds to be compared for their cytotoxic effects on one, or a plurality, of proliferating target cell lineages. To these ends, a plurality of hematopoietic stem or progenitor cell populations may, for example, be plated in the wells of a multi-well plate or in individual chambers, thereby allowing rapid testing of multiple samples.

The high-throughput assays of the present invention may be used to determine the ability of a test compound to increase the proliferation of a population of hematopoietic stem or progenitor cells. Such proliferation enhancing compounds include, for example, cytokines and growth factors.

The assay methods of the present invention may also be used with a range of concentrations of the test compound which may be contacted with a plurality of cell populations of the same cell lineage, whereupon the IC50 or the IC90 for the test compound acting against the targeted cell population or a subpopulation thereof may be calculated.

High-throughput Assay Methods for Screening Hematopoietic Stem and Progenitor Cell Populations for Suitability for Transplantation The high-throughput assay methods of the present invention are also suitable for screening a population of hematopoietic stem or progenitor cells to determine the proliferation status of the cells or subpopulations thereof wherein the proliferative status will indicate the suitability of the stem or progenitor cells for transplantation into a recipient animal or human host. The high-throughput assay of the present invention will allow the selection of populations of primitive hematopoietic cell that will likely proliferate and maintain engraftment within the recipient patient.

High-throughput Assay Methods for Determining the Proliferative Status of a Target Cell Population In the methods of the present invention as described, for example, in Examples 1 and 2 below, target hematopoietic stem and/or progenitor cells may be isolated from animal or human tissues and suspended at cell concentrations ranging from about $1-5 \times 10^2$ to about $1-2 \times 10^5$/ml. Since typical assay volumes are 100 µl, actual cell concentrations in the assay test vessels may be diluted to ⅒ of the original starting cell concentration. The cells are mixed and suspended in methyl cellulose containing 0% to about 30% concentration of fetal bovine serum (FBS), 1% detoxified bovine serum albumin (BSA), iron-saturated human transferrin at a final concentration of $1 \times 10^{-10}$ mol/L, α-thioglycerol at a final concentration of $1 \times 10^{-4}$ mol/L and cytokines/growth factors. The methyl cellulose concentration in the assays of the present invention is between about 0.4% and about 0.7%, with a preferred concentration for most cell populations of about 0.7%. One exemplary medium is Iscove's Modified Dulbecco's Medium (IMDM, Life Technologies, Rockville, Md.) although other suitable media capable of supporting the growth of hematopoietic cells may also be used. Low fetal bovine serum concentrations of between 0% and 10% can also be used. When the assay methods of the present invention are used under serum-free conditions, insulin (10 µg/ml) and, where necessary, low density lipoproteins (40 µg/ml) can replace the FBS.

For example, in the basic method of the present invention, as described in Example 1 below, Iscove's Modified Dulbecco's Medium (IMDM) obtained from Invitrogen/Gibco (Carlsbad, Calif.) is prepared in small amounts (100-150 ml) using sterilized, 17.3 MOhm water. A 1.75% methyl cellulose stock solution containing alpha-thioglycerol was prepared in IMDM. The volumes of all reagents are dependent upon the final volume(s) required for the study. The final volume of reagents is, in turn, dependent on the amount of methyl cellulose that can be dispensed in multiples of standard volumes using a repeater syringe. The components may be dispensed into tubes using electronic pipettes as follows: 5% FBS, 20% BIT, growth factors, methyl cellulose and IMDM. The components are thoroughly mixed on a vortex mixer and cells are added and mixed again. The tubes are centrifuged briefly to 500 rpm so that the components are removed from the walls of the tubes. 100 µl of reagent mix is dispensed into replicate wells of a white, multi-well plate. The luminescence plate has a clear base so that cell growth can be observed under the inverted microscope.

Culture plates are incubated at 37° Celsius in a humidified atmosphere containing 5% $CO_2$ and 5% $O_2$. On the day of analysis, the plates are transferred to a humidified incubator with 5% $CO_2$ at 22° Celsius to equilibrate. Reagents for ATP determination.

Using a multichannel pipette, 125 µl of ATP-releasing reagent (ATP releasing reagent) is added to each well, mixed and returned to the 22° Celsius incubator for 15 mins. Thereafter, 20 µl of ATP luminescence-monitoring reagent (ATP luminescence-monitoring reagent) is added and the luminescence read immediately. Data from the plate reader is used to calculate the mean, standard deviation and percent variation automatically for graphical presentation and/or statistical evaluation respectively. For all assays, a 10 µM ATP standard can be performed on the day of analysis to provide quality control for the reagents and equipment as well as a reference to which all values can be calculated.

The high-throughput assay method of the present invention further includes contacting a hematopoietic stem or progenitor cell population with at least one cytokine that can induce the proliferation of the stem or progenitor cell population. The cytokine, or a combination of cytokines, may be selected to induce the differentiation and proliferation of selected subpopulations of, for example, hematopoietic cell lineages. Exemplary cytokines include, but are not limited to erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor. Additional growth factors, alone or in combination, may also be included to boost the proliferative status of a particular culture of cells, including such factors as insulin-like growth factor, insulin and recombinant insulin. Examples of cytokines or combinations thereof that may be used in the assay methods of the present invention and the specific targeted stem, progenitor or precursor cell types, and the resulting expanded cell lineages are given in Example 3 and Table 3 below.

The stock cell culture is aliquoted into sample chambers. While sample chambers may be the wells of a multi-well tissue culture plate, and preferably a or 96-well plate, it is also contemplated to be within the scope of the present invention to conduct the assays of the present invention in any other suitable reaction vessels including, but not limited to, individual tubes, wells of plates and the like. Culture plates with a well surface area of about 35 mm² and a low ring of about 2 mm high are especially useful and allow colonies to be counted that are against the wall of the ring. Preferably the sample chambers are not tissue culture treated.

Plastic that is sterilized and tissue culture treated exhibits different surface properties than plastic that is not sterilized by radiation and not tissue cultured treated. The change in surface properties results in cells preferentially adhering to the plastic and growing more rapidly than colony-forming cells. This is especially true if the cell suspension contains macrophages and other microenvironmental cell components. Also, the surfaces of individual wells of a multi-well plate may not be treated homogenously and may result in complete growth inhibition in a significant number of wells. This can be a random event such that although 8-12 replicates may have been plated, up to 5 wells on a single plate might exhibit no growth whatsoever. Unwanted preferential adherence and growth may be avoided by using "non-sterile" and untreated plates. All tissue culture articles made from "virgin" plastic under very high temperatures, when released from the mold, are sterile. Contamination problems are unlikely. Non-treated and non-irradiated plates allow superior growth for the methods of the present application.

For luminescence assays to be performed, multi-well plates that reduce background light emission or scatter when the plates are being enumerated in the plate reader may also be used. While it is desirable to use replicate reactions, it is to be understood that a single reaction sample may be used for determining the proliferative status of cells for each data point. However, replicate reactions are to be preferred wherever an increase in accuracy is necessary. For example, reactions may be replicated once, twice or more times, including on a single multi-well plate, although quadruple reactions are preferred.

The cultures can be incubated in a humidified atmosphere having a low oxygen tension for a period preferably extending to about 10 days but also to at least about 14 days. A suitable oxygen concentration range is from about 3.5% oxygen to about 7.5% oxygen, most preferably about 5.0% oxygen, and further comprising about 5% $CO_2$ as described by Bradley et al. (*J. Cell Physiol.* 97, 517-522 (1968) and Rich & Kubanek (*Exp. Hemat.* 52, 579-588 (1982) incorporated herein by reference in their entireties.

Regardless of the instrument parameters used, there is a direct correlation between the cell concentration plated in the wells and the mean, or sum, of the relative luminescence units obtained, as shown in Example 4, below. To avoid large standard deviations, an integration time of 1000 ms may be used, although other integration times may usefully be selected.

By determining the sum or mean of the relative luminescence units (RLU) in all replicates of a single sample at a specified time point during the incubation procedure, for example at 4, 7, 10 or 14 days of incubation, the assay can be used to rapidly and quantitatively determine: (a) the proliferative status of a hematopoietic stem or progenitor cell population or of cells of a specific progenitor and differentiation lineage and compare such in parallel assays; (b) if cells from a particular source exhibit a normal or abnormal proliferative capacity; and (c) whether a compound (e.g. growth factor, cytokine, drug, neutraceutical, environmental agent), will have a positive or negative effect of the proliferative status of the cells in a particular cell population. The assay, even of multiple samples, can be completed within 30 min, calculated from the time of adding the ATP releasing agent to the conclusion of the luminescence measurement.

A high-throughput stem/progenitor cell assay (HT-SPCA) of the present invention does not count colonies or differentiate between colony types. Rather, the HT-SPCA of the present invention measures the proliferation status of cells within the colonies by determining the amount of ATP being produced by the cells. With colony growth in the methyl cellulose assay system of the present invention, some cells in the cultures will begin to proliferate and form aggregates or clusters. However, the proliferative status of the cell population may be limited due to their late stage of differentiation. Thus, a small colony may ensue within a short incubation period, but cell proliferation will rapidly cease.

In the assay methods of the present invention, the culture conditions include α-thioglycerol to maintain molecules in a reduced form, and the cultures are incubated under low oxygen tension of between about 3.5% oxygen and about 7.5% oxygen, both conditions reducing oxygen toxicity. The cell aggregate or colony can be maintained in a stagnant or non-proliferative state for between about 2 and about 3 weeks. Other cells, however, that are developmentally more primitive, for example, stem and progenitor cells, have a greater proliferative capacity and will begin to form colonies after a certain lag period of time. These cells will continue to divide throughout the whole of the incubation period. Eventually, the proliferative capacity of the cells within these colonies will also decrease and finally cease.

In one embodiment of the method of the present invention, the concentration of fetal bovine serum is between about 0% and 10%.

In another embodiment of the method of the present invention, the concentration of methyl cellulose is about 0.7%.

In yet another embodiment of the present invention, the concentration of oxygen in the atmosphere is about 5%.

Another embodiment of the method of the present invention further comprises the step of contacting a target cell population with at least one cytokine and optionally may further comprise the step of generating a cell population enriched in hematopoietic stem cells.

One embodiment of the method of the present invention comprises the step of generating a target cell population enriched in at least one hematopoietic progenitor cell lineage.

In one embodiment of the method of the present invention, the primitive hematopoietic cells are hematopoietic stem cells.

In another embodiment of the method of the present invention, the primitive hematopoietic cells are hematopoietic progenitor cells.

In yet another embodiment of the method of the present invention, the population of primitive hematopoietic cells comprises hematopoietic stem cells and hematopoietic progenitor cells.

In still another embodiment of the method of the present invention, the primitive hematopoietic cells are primary hematopoietic cells.

In one embodiment of the method of the present invention, the target cell population is isolated from animal tissue selected from the group consisting of peripheral blood, bone marrow, umbilical cord blood, yolk sac, fetal liver and spleen.

In one embodiment of the method of the present invention, the animal tissue is obtained from a human.

In one embodiment of the method of the present invention, the animal tissue is selected from bone marrow, yolk sac, fetal liver and spleen.

In various embodiments of the method of the present invention, the animal is a mammal.

In various embodiments of the method of the present invention, the mammal is selected from the group consisting of cow, sheep, pig, horse, goat, dog, cat, non-human primates, rodents, rabbit and hare.

In another embodiment of the method of the present invention, the animal tissue is human tissue further selected from the group consisting of peripheral blood, bone marrow, and umbilical cord.

In yet another embodiment of the method of the present invention, the primary hematopoietic stem cells are isolated from peripheral blood.

Still another embodiment of the method of the present invention further comprises the step of selecting a differentially distinguishable subpopulation of primitive hematopoietic cells from the population of primitive hematopoietic cells, wherein the subpopulation of cells is defined by cell surface markers thereon.

In one embodiment of the method of the present invention, the step of selecting a differentially distinguishable subpopulation of primitive hematopoietic cells from the population of primitive hematopoietic cells comprises the steps of contacting the population of primitive hematopoietic cells with a cell surface marker indicator capable of selectively binding to a cell surface marker of a differentially distinguishable subpopulation of cells, and selectively isolating the subpopulation of cells binding the at least one indicator.

In one embodiment of the method of the present invention, the cell surface marker is selected from the group consisting of CD3, CD4, CD8, CD34, CD90 (Thy-1) antigen, CD117, CD38, CD56, CD61, CD41, glycophorin A, HLA-DR, CD133 defining a subset of CD34$^+$ cells, CD19, and HLA-DR.

In one embodiment of the method of the present invention, the cell surface marker is CD34$^+$.

In one embodiment of the method of the present invention, the subpopulation of differentially distinguishable primitive cells is selectively isolated by magnetic bead separation.

In another embodiment of the method of the present invention, the subpopulation of differentially distinguishable primitive cells is selectively isolated by flow cytometry and cell sorting.

In yet another embodiment of the method of the present invention, the population of primitive hematopoietic cells comprises at least one stem cell lineage selected from the group consisting of colony-forming cell-blast (CFC-blast), high proliferative potential colony forming cell (HPP-CFC) colony-forming unit-granulocyte, erythroid, macrophage, megakaryocyte (CFU-GEMM).

In the various embodiments of the methods of the present invention, the population of primitive hematopoietic cells comprises at least one hematopoietic progenitor cell lineage selected from the group consisting of granulocyte-macrophage colony-forming cell (GM-CFC), megakaryocyte colony-forming cell (Mk-CFC), macrophage colony-forming cell (M-CFC), granulocyte colony forming cell (G-CFC), burst-forming unit erythroid (BFU-E), colony-forming unit-erythroid (CFU-E), colony-forming cell-basophil (CFC-Bas), colony-forming cell-eosinophil (CFC-Eo), B cell colony-forming cell (B-CFC) and T cell colony-forming cell (T-CFC).

Also, in the various embodiments of the methods of the present invention, the reagent capable of generating luminescence in the presence of ATP comprises luciferin and luciferase.

Also, in the various embodiments of the methods of the present invention, the cytokine is selected from the group consisting of erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor and combinations thereof.

In one embodiment of the method of the present invention, the at least one cytokine is stem cell factor, interleukin-6 and Flt3L.

In another embodiment of the method of the present invention, the at least one cytokine is macrophage colony stimulating factor, interleukin-1, interleukin-3, interleukin-6 and stem cell factor.

In yet another embodiment of the method of the present invention, the at least one cytokine is erythropoietin, granulocyte-macrophage colony stimulating factor, granulocyte colony stimulating factor, stem cell factor, interleukin-3, interleukin-6, and stem cell factor and Flt3L.

In still another embodiment of the method of the present invention, the at least one cytokine is selected from the group consisting of erythropoietin, erythropoietin and interleukin-3, erythropoietin and stem cell factor and erythropoietin, stem cell factor and interleukin-3.

In still yet embodiment of the method of the present invention, the at least one cytokine is further selected from granulocyte-macrophage colony stimulating factor, granulocyte-macrophage colony stimulating factor and interleukin-3, and granulocyte-macrophage colony stimulating factor, interleukin-3 and stem cell factor.

In another embodiment of the method of the present invention, the at least one cytokine is further selected from the groups consisting of thrombopoietin, and thrombopoietin, interleukin-3 and interleukin-6.

In yet another embodiment of the method of the present invention, the at least one cytokine is further selected from interleukin-2, and interleukin-7, Flt3L and interleukin-15.

In still another embodiment of the method of the present invention, the at least one cytokine is selected from the group consisting of interleukin-7, and interleukin-7 and Flt3L.

In still yet another embodiment of the method of the present invention, the at least one cytokine is erythropoietin.

In another embodiment of the method of the present invention, the at least one cytokine is selected from the group consisting of granulocyte-colony stimulating factor and granulocyte-macrophage colony stimulating factor.

In yet another embodiment of the method of the present invention, the at least one cytokine is selected from the group consisting of interleukin-3, and interleukin-3 and stem cell factor.

In still another embodiment of the method of the present invention, the at least one cytokine is selected from the group consisting of granulocyte-macrophage colony stimulating factor, interleukin-3 and interleukin-5.

In still yet another embodiment of the method of the present invention, the at least one cytokine is selected from the group consisting of macrophage colony stimulating factor, macrophage colony stimulating factor and granulocyte-macrophage colony stimulating factor and interleukin-3, and granulocyte-macrophage colony stimulating factor.

One embodiment of the method of the present invention further comprises the step of identifying a population of primitive hematopoietic cells having a proliferative status suitable for transplantation into a recipient patient.

Another aspect of the present invention, therefore, is a high-throughput assay method for rapidly identifying a population of having a proliferative status suitable for transplantation into a patient, comprising the steps providing a cell population comprising primitive hematopoietic cells, incubating the cell population in cell a growth medium comprising between 0% and 30% fetal bovine serum and a concentration of methyl cellulose between about 0.4% and about 0.7%, and in an atmosphere having between about 3.5% and about 7.5% oxygen, contacting the primitive hematopoietic cell population with at least one cytokine selected from the group consisting of erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor, insulin-like growth factor, and insulin, contacting the cell population with a reagent capable of generating luminescence in the presence of ATP, and detecting luminescence generated by the reagent contacting the at least two cell populations, the level of luminescence indicating the proliferative status of the primitive hematopoietic cells, and wherein the proliferative status of the primitive hematopoietic cells indicates the suitability of the cell population for transplantation into a recipient patient.

In one embodiment of this aspect of the method of the present invention, contacting the target cell population with at least one cytokine generates a cell population enriched in a stem cell lineage, such as a hematopoietic stem cell lineage.

In one embodiment of the method of the present invention, the hematopoietic stem cell lineage is selected from the group consisting of colony-forming cell-blast (CFC-blast), high proliferative potential colony forming cell (HPP-CFC) colony-forming unit-granulocyte, erythroid, macrophage, megakaryocyte (CFU-GEMM).

In another embodiment of this aspect of the method of the present invention, contacting the target cell population of with a cytokine generates a cell population enriched in at least one hematopoietic progenitor cell lineage.

In the various embodiments of this aspect of the method of the present invention, the population of primitive hematopoietic cells comprises at least one hematopoietic progenitor cell lineage selected from the group consisting of granulocyte-macrophage colony-forming cell (GM-CFC), megakaryocyte colony-forming cell (Mk-CFC), macrophage colony-forming cell (M-CFC), granulocyte colony forming cell (G-CFC), burst-forming unit erythroid (BFU-E), colony-forming unit-erythroid (CFU-E), colony-forming cell-basophil (CFC-Bas), colony-forming cell-eosinophil (CFC-Eo), B cell colony-forming cell (B-CFC) and T cell colony-forming cell (T-CFC).

Yet another aspect of the present invention is a high-throughput assay method for rapidly identifying a compound capable of modulating the proliferative status of a population of primitive hematopoietic cells, comprising providing target cell population, incubating the cell population in cell a growth medium comprising between 0% and 30% fetal bovine serum and a concentration of methyl cellulose between about 0.4% and about 0.7%, and in an atmosphere having between about 3.5% and about 7.5% oxygen, contacting the target cell populations with at least one cytokine selected from the group consisting of erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor, insulin-like growth factor, and insulin, providing a first and a second target cell populations, contacting the first target cell population with a test compound, contacting the first and second target cell populations with a reagent capable of generating luminescence in the presence of ATP, detecting luminescence generated by the reagent contacting the first and second target cell populations, the level of luminescence indicating the proliferative status of the first and second target cell populations, and comparing the proliferative status of the second target cell population with the proliferative status of the first target cell population of primitive hematopoietic cells, thereby identifying a test compound capable of modulating the proliferative status of a target cell population.

In the various embodiments of this aspect of the method of the present invention, contacting the first and second target cell populations with a cytokine that generates a cell population enriched in hematopoietic stem cells.

In other embodiments of the methods of the present invention, the hematopoietic stem cells are selected from the group consisting of colony-forming cell-blast (CFC-blast), high proliferative potential colony forming cell (HPP-CFC) colony-forming unit-granulocyte, erythroid, macrophage, megakaryocyte (CFU-GEMM).

Also, in the various embodiments of this aspect of the method of the present invention, contacting the first and second target cell populations of primitive hematopoietic cells with at least one cytokine generates cell populations enriched in at least one hematopoietic progenitor cell lineage.

In the various embodiments of this aspect of the method of the present invention, the at least one hematopoietic progenitor cell lineage selected from the group consisting of granulocyte-macrophage colony-forming cell (GM-CFC), megakaryocyte colony-forming cell (Mk-CFC), macrophage colony-forming cell (M-CFC), granulocyte colony forming cell (G-CFC), burst-forming unit erythroid (BFU-E), colony-forming unit-erythroid (CFU-E), colony-forming cell-basophil (CFC-Bas), colony-forming cell-eosinophil (CFC-Eo), B cell colony-forming cell (B-CFC) and T cell colony-forming cell (T-CFC).

One embodiment of the method of the present invention further comprises the steps of contacting a target cell population with at least two concentrations of a test compound, and calculating the IC50 of the test compound.

Another embodiment of the method of the present invention further comprises the steps of contacting a target cell population with at least two concentrations of a test compound and calculating the IC90 of the test compound.

HALO-related Method Kits.

The present invention provides the HALO method technology in kit form and is useful for applications for research purposes, or clinical applications. Reducing the complexity of assay staging by minimizing the number of components involved allows the HALO platform to be used by individuals at any experience level. The kits of the present invention provide the components and instructions for their use in the HALO procedure, thereby providing an easy to use, flexible assay system whereby the effects of both positive and negative regulators of hematopoiesis can be studied using a number of different cell populations, in different species of interest.

In the HALO methods that form the basis of the kits of the present invention, ATP is released from the cells using ATP-releasing reagent and a 15 min incubation. Thereafter, the ATP luminescence-monitoring reagent is added and the plates read immediately. Thirty minutes later, an ADP converting reagent (ADP-CR) is added which converts ATP to ADP and the plates are read every 5 mins for a further 15-20 mins. Three values are then used to calculate the kinetics of the reaction. The first reading (A) is that immediately after addition of ATP luminescence-monitoring reagent. The second reading (B) is just prior to addition of ADP-CR, when the decline in ATP is maximal. The third reading (C) is taken at a time when the conversion of ADP to ATP has reached a plateau. The ADP:ATP ratio is then calculated from the simple equation: (C−B)/A. This procedure was performed to obtain the results shown in FIG. 16. The procedure is preferably performed by the automatic addition of ATP luminescence-monitoring reagent and ADP-CR using a luminometer equipped with two injectors.

To stimulate the robust proliferation of various target lineages, a plating mixture may be necessary that has as many as 14 components, including the cells. Once assembled and mixed, these plating mixtures must then be divided into replicate wells of a multiple-well plate, and the cells allowed to grow. Although this approach retains maximum flexibility, it also requires much repetitive pipetting of individual components, particularly when several different lineages were plated side by side, as was typical. This approach is time consuming and error prone. Minimizing the number of reagent additions increases the speed with which assays can be performed, lowers assay-to-assay variation, and at the same time, decreases the likelihood of contamination, while creating a more robust and reproducible assay platform. Furthermore, assay staging is also more amenable to automation.

By identifying reduced serum conditions which support the expansion of many target cells and lineages, the assay staging pre-combines serum and serum replacement components, such that addition of a "serum" cocktail in a single standardized volume, compatible with the same repeating syringe dispensers described above, results in the desired concentrations of each component in each final plating mixture being assembled. This assay component is designated BITSI. Its preferred composition is Bovine serum albumin (50 mg/ml), recombinant human Insulin (50 µg/ml) iron-saturated Transferrin (1 mg/ml), Serum, and IMDM, although it is contemplated that the amounts and final concentrations of the individual components of BITSI may be varied in accordance with the requirements of a particular cell line being cultured The bovine serum albumin, insulin and transferrin may be a single reagent (for example, BIT, Stem Cell Technologies, Vancouver, Canada), that is combined in a 4:1:3 ratio with serum and IMDM respectively. This reduces the amount of IMDM that must be added separately to each final plating mixture, and also standardizes the volume of BITSI required to one that can be dispensed with positive displacement syringe dispensers. For human and non-human primate cells, FBS pre-screened for human cell growth can be used, whereas for mouse and rat cells, FBS pre-screened for murine cell growth is preferred. In each case, a final assay concentration of 5% serum/20% BIT is achieved.

Combinations of growth factors may be used to stimulate the proliferation of each lineage tested using the HALO procedure. For example, 6 different growth factors are required to stimulate the proliferation of CFC-GEMM, and three different growth factors are required to stimulate the proliferation of BFUe, GM-CFC and Mk-CFC. Each of the growth factors required for a particular lineage can be combined, in appropriate proportions, into a lineage-specific growth factor mix, thereby thereby obviating the need to add each of the required growth factors separately. A combination of IL-3, IL-6, SCF, GM-CSF, EPO, and G-CSF, added respectively at, for example, doses of 1, 2, 3, 4, 10 and 20 ul per ml of plating mixture, can be used to stimulate the proliferation of CFC-GEMM. 40 µl of this GEMM-specific cocktail would be required for each 1 ml of lineage-specific plating mixture being prepared. Similarly, for BFU-E, IL-3, SCF, and EPO, respectively at doses of 1, 3 and 10 ul per ml of plating mixture, could be premixed and 14 µl of the resulting BFU-E-specific cocktail would be required per ml of plating mixture being prepared. Also, for example, 8 µl of a 1:3:4 premix of IL-3, SCF, and GM-CSF is used to stimulate the proliferation of GM-CFC, and 5 µl of a 1:2:2 premix of IL-3, IL-6 and TPO would be used to stimulate the proliferation of Mk-CFC. Large volumes of pre-mixed growth factor combinations are provided by the kits of the present invention, aliquoted, and frozen ready for use The kits of the present invention, therefore, provide lineage-specific plating mixtures from three premixed reagent mixes, each mix preferably provided in separate vessels (i.e. 2.5× methyl cellulose, a 1.75% methyl cellulose base may contain 2.5× final concentration of α-thioglycerol, BITSI reagent, growth factor cocktails). Volumes of each mix vary depending upon the final volume of plating mixture required for each lineage under test. An additional component to be added to the final mix, is a standardized volume of cell suspension containing a predetermined concentration of target cells, and sufficient IMDM to take account of variations in the volume of growth factor cocktails added to different lineages, thereby adjusting each plating mixture to an appropriate final volume. The kits may further comprise a luminescence plate that, preferably, is a non-treated, non-sterile multi-well plate. The kits of the present invention also comprise instructions for the use of the kit in preparing and performing the HALO procedure.

Purely in terms of liquid handling, the HALO procedure comprises the following stages: (i) assembly of lineage-specific plating mixtures from liquid components, i.e. BITSI, growth factor cocktails, target cells and medium; (ii) addition of methyl cellulose/α-TG mix using positive displacement liquid handling devices; (iii) distributing of aliquots, for example, 100 µl, of each plating mixture onto multi-well plates using positive-displacement liquid handling devices; (iv) addition of ATP releasing reagent to each of the culture wells; (v) addition of ATP luminescence-monitoring reagent to each of the culture wells; and (vi) addition of ATP-CR to each of the culture wells if apoptosis is to be measured.

Once the mixes of the kits of the present invention have been combined in accordance with the instructions of the kits, automation may be applied using currently available laboratory robotics and liquid handling technology. However, manual use of disposable positive-displacement repeating syringe dispensers during the addition of stock methyl cellulose to plating mixtures, and for subsequent plating of those mixtures can be reliable and a cost effective alternative to full automation. Stages (i) and (iv) are can be performed using automated liquid handling workstations, and stages (v) and (vi) can be performed using a luminometer equipped with reagent injectors.

The liquid handling workstation should be confined during this part of the procedure to a sterile environment, either by containing such a workstation within a laminar flow hood, or by using it only within the confines of a separate clean room supplied with positive pressure HEPA-filtered air. The liquid handling workstation should, therefore have a footprint small enough to allow enclosure within a laminar air-flow hood. In addition, any such workstation should be capable of (a) using sterile tips capable of dispensing a wide range of sample volumes, (b) transferring reagents to and from tubes, and to 96 well plates and (c) dispensing ATP releasing reagent using either 8-tip, 12-tip or 96-tip manifolds. Given the fact that Methyl cellulose stocks and Methyl cellulose-containing plating mixtures can easily be dispensed using a repeater pipettes and disposable sterile syringe tips, with great accuracy and reproducibility, and at a fraction of the cost, use of a positive displacement liquid handling workstation is desirable, but not essential.

A semi-automated embodiment of the HALO procedure of the present invention, would be as follows. Firstly, liquid reagent cocktails, i.e. BITSI and lineage-specific growth factor cocktails, cell suspensions, and medium are assembled into an appropriate number of lineage-specific plating mixtures, optionally using an automated liquid handling workstation. Aliquots of a 2.5× methyl cellulose/α-TG mix may be added manually to these plating mixtures, using a repeater pipette and a disposable positive-displacement syringe tip. Having thoroughly mixed the plating mixtures, 100 µl aliquots of each would then be dispensed manually, again using a repeater pipette and disposable syringe tips, onto 96-well plates containing agents under test in appropriate concentration ranges. After incubating assay plates for an appropriate length of time, aliquots of ATP releasing reagent would be added to the wells of each plate under test, using a robotic liquid handling workstation. Plates would be incubated at room temperature for 15 minutes as per manual assays, and would then be transferred to an injector-equipped luminometer, where of ATP luminescence-monitoring reagent would be injected automatically into each well immediately prior to measurement of ATP-generated bioluminescence. If apoptosis measurements were also to be made, aliquots of ATP-CR would subsequently be injected automatically (from a second injector), and the concomitant conversion of ADP to ATP measured over time. Automating the ATP measurement stage of the assay improves the high-output capacity of the assay system. Similarly, partially automating the "front-end" of the assay significantly increases the throughput of assay plates.

The present invention is further illustrated by the following examples, which are provided by way of illustration and should not be construed as limiting. The contents of all references, published patents and patents cited throughout the present application are hereby incorporated by reference in their entirety.

EXAMPLE 1

Hematopoietic and Hematotoxicity Assay via Luminescence Output (HALO)

Step 1: Cell Preparation

The type of HALO kit used is determined according to which stem and/or progenitor cell populations are to be detected and whether for human or murine hematopoietic cells. If the kits of the present invention are defined for use with human cells, it can also be used to culture non-human primate (both rhesus and cynmologus primates) and canine hematopoietic cells. If the kits are defined for use with mouse cells, they can also be used to culture rat hematopoietic cells.

A. Murine or Rat Bone Marrow
1. Remove organs (femora or tibia) under aseptic conditions.
2. Remove as much muscle from the bones as possible.
3. Using a sterile sharp blade, first cut off the proximal (hip joint) end below the ball joint at right angles to the longitudinal length of the bone. Then cut off the distal end (above the patella or knee).
4. Transfer sufficient medium to a tube so that it will cover the whole bone. (Some of the medium provided with the kit can be used for this purpose).
5. Half fill a syringe (1-3 ml) with medium and, using a needle gauge that will enter the bone cavity without cracking the bone, insert the needle into the proximal end and immerse the whole bone in the medium contained in the tube.
6. Flush out the marrow through the bone cavity and withdraw part of the cell suspension through the bone and into the syringe.
7. Flush the cell suspension through the bone and repeat steps 6 and 7 two to three times. When finished, the bone should appear translucent, indicating that most of the cells have been flushed out of the cavity.
8. Remove the empty bone and replace it with the next bone until the marrow from all bones has been flushed out of the cavities.
9. Let the cell suspension settle for 1-2 minutes to allow large debris to fall to the bottom of the tube.
10. Using a small gauge (22-25) needle, slowly withdraw the cell suspension and transfer it to a new tube, noting the volume.
11. If necessary, add medium to achieve the required volume.
12. Determine the cell concentration using either a hemocytometer or electronic cell/particle counter.

B. Human Cells
1. Regardless of whether peripheral blood (PB), bone marrow (BM) or umbilical cord blood (CB) is used, dilute the sample 1:1 with sterile phosphate buffered saline (PBS).
2. Remove the density gradient separation medium (DGSM, e.g. Ficoll-Paque Plus, Pharmacia) from the fridge and allow it to equilibrate to room temperature.
3. Transfer 15 ml of DGSM to a 50 ml sterile, plastic, screw top tube. (15 ml can be used for up to 35 ml of 1:1 diluted blood tissue).
4. Tilt this tube to approx. 45° and, using a 10 ml sterile pipette, layer the diluted cells on top taking care not to mix the DGSM with the cells.
5. Once all the cells have been layered in this-way, centrifuge the tube(s) at 400×g for 25 min at room temperature without using the centrifuge brake to slow the rotor.
6. Carefully remove the tubes from the centrifuge without mixing the contents and aspirate the upper diluted plasma layer to approximately 5-10 mm above the interface with the DGSM. The interface contains the mononuclear cells.
7. Using a sterile 5 ml or 10 ml pipette, remove the ring of cells at the interface as well as the medium below the interface to about 10-20 mm above the red blood cell pellet at the bottom of the tube, and transfer the cells to a new 50 ml sterile tube.
8. Fill this tube to 50 ml with sterile PBS, gently mix by inverting the tube several times and centrifuge again at 200×g for 10 min at room temperature.
9. Aspirate and discard the supernatant to just above the cell pellet and resuspend the cells in a specific amount of medium. (Medium provided with the kit can be used for this purpose).
10. Determine the cell concentration by manual means using a hemocytometer or using an electronic cell/particle counter.

C. Non-human Primate and Canine Peripheral Blood and Bone Marrow

Both of these sources need to be processed in the same manner as human cells to separate the mononuclear cell fraction. The same protocol can be followed if non-human primate or canine hematopoietic tissue, but ensure that the correct density-gradient medium is used to separate the mononuclear cells from different species.

D. Isolation of Hematopoietic Subpopulations

Subpopulations of stem and progenitor cells can be isolated and used in the procedure of the present invention. We recommend using magnetic cell isolation procedures, since these allow rapid isolation of different cell populations with substantial purity, viability and yield. Recommended cell concentrations to determine the optimal final cell concentration to use in the HALO procedure of the present invention are shown in Table 1 below.

with needles may result in inaccurate dispensing and greater variation between replicate wells.

Number of replicates performed: At least 4 replicates per culture point are preferred.

Plate configuration: The configuration of the 96-well plate for an experiment is arbitrary. However, the number of replicates and the way in which the reagents required to measure luminescence are added, will determine the plate configuration. For example, if performing 4 or 8 replicates per culture point, we recommend configuring the plate in columns, that is, A1 to D1 and E1 to H1 etc. for quadruplicate cultures and A1 to H1, A2 to H2 etc. for 8-replicate cultures are possible. If performing 6 or 12 replicates, we

TABLE 1

Recommended Cell Concentrations for Different Species, Cell Types, Cell Preparations and Cell States for the HALO Platform

| Species | Cell type | Cell preparation | Cell state | Working cell concentration required | Final cell concentration per well. |
|---|---|---|---|---|---|
| Mouse | Bone marrow | Whole | Fresh | $1–2 \times 10^6$/ml | $1–2 \times 10^4$/well |
|  | Spleen | Whole | Fresh | $2–3 \times 10^6$/ml | $2–3 \times 10^4$/well |
| Rat | Bone marrow | Whole | Fresh | $2 \times 10^6$/ml | $2 \times 10^4$/well |
| Dog | Bone marrow | MNC | Fresh | $2 \times 10^6$/ml | $2 \times 10^4$/well |
|  | Bone marrow | MNC | Frozen | $2 \times 10^6$/ml | $2 \times 10^4$/well |
| Non-human primate | Bone marrow | MNC | Fresh | $2 \times 10^6$/ml | $2 \times 10^4$/well |
|  | Bone marrow | MNC | Frozen | $2 \times 10^6$/ml | $2 \times 10^4$/well |
| Human | Bone marrow | MNC | Fresh | $1–2 \times 10^6$/ml | $1–2 \times 10^4$/well |
|  | Peripheral blood | MNC | Fresh | $2 \times 10^6$/ml | $2 \times 10^4$/well |
|  | Umbilical cord blood | MNC | Fresh | $0.5–1 \times 10^6$/ml | $0.5–1 \times 10^4$/well |
|  | Bone marrow | MNC | Frozen | $1–2 \times 10^6$/ml | $1–2 \times 10^4$/well |
|  | Peripheral blood | MNC | Frozen | $2 \times 10^6$/ml | $2 \times 10^4$/well |
|  | Umbilical cord blood | MNC | Frozen | $0.5–1 \times 10^6$/ml | $0.5–1 \times 10^4$/well |
|  | Bone marrow | CD34$^+$ | Fresh | $1 \times 10^5$/ml | $1 \times 10^3$/well |
|  | Umbilical cord blood | CD34$^+$ | Fresh | $0.1–1 \times 10^5$/ml | $0.1–1 \times 10^3$/well |

If cells have been treated prior to cell culture, high cell concentrations may be required.

Step 2: HALO Preparation and Cell Culture

Depending on the type and size of the HALO kit used, all of the culture components required, with the exception of the cells, are included. A typical HALO kit contains the 3 component mixes required to culture cells:

1. Serum component mix (Mix 1)
2. Methyl cellulose mix (Mix 2)
3. Growth factor mix (Mix 3)
4. Cells prepared as in step 1 above.

Methyl cellulose provided: Methyl cellulose is a viscous, water soluble, semi-solid medium for immobilizing cells. The amount of methyl cellulose provided is for the number of 96-well plates determined by the kit. However, if dispensed carefully, there is sufficient methyl cellulose so that several smaller experiments can be performed using the plate(s) provided.

Dispensing individual component mixes and reagents: A repeater pipette may be used which uses a positive-displacement syringe is used to dispense the methyl cellulose mix.

Dispensing the master mix: Once all the component mixes have been added together, a repeater pipette to dispense the master mix into individual wells. Using normal syringes recommend configuring the plate in rows, that is, A1-A6 and A7 to A12 for 6 replicates and A1-A12, B1 to B13 for 12 replicates are possible. If performing column replicates, addition of the ATP releasing reagent and ATP luminescence-monitoring reagent can be performed using an 8-channel pipette from left to right across the plate. If performing row replicates, an 8- or 12-channel pipette can be used to dispense the reagents from the top to the bottom of the plate.

To calculate the quantities of reagents required:

1. Determine the number of sample categories required for testing and the number of replicates for each sample.
2. Multiply the number of sample categories by the number of replicates to obtain the number of wells to be used.

Total number of wells=Number of sample categories×Number of replicates

3. Multiply the number of wells to be used by 100 μl (volume of each well) plus an extra 20%. This will give the total volume required.

Total volume (μl) to be prepared=(Number of wells× 100 μl)+20%.

4. Determine and label the number and types of tubes required for the number of samples and replicates. Total volumes of 3,500 μl (3.5 ml) or less should be prepared in sterile 5 ml plastic tubes with caps. Volumes greater than 3,500 μl (3.5 ml), but less than 9,500 μl (9.5 ml) should use 10-12 ml sterile plastic tubes. Volumes greater than 9,500 μl (9.5 ml) should use 50 ml sterile plastic tubes. If using sufficient reagents to prepare 1 batch for all 96-wells, use a 10 ml tube.

5. For each sample tube, mix the following components in the ratios shown below:

| Component | Number of parts |
| --- | --- |
| Mix 1 (serum component mix) | 4 |
| Mix 2 (methyl cellulose mix) | 4 |
| Mix 3 (growth factor mix) | 1 |
| Cells | 1 |

For example, if a total volume of 1000 μl (1.0 ml) is required, the following volumes would be necessary:

| Component | Number of parts | Volumes (μl) |
| --- | --- | --- |
| Mix 1 (serum component mix) | 4 | 400 |
| Mix 2 (methyl cellulose mix) | 4 | 400 |
| Mix 3 (growth factor mix) | 1 | 100 |
| Cells (at required cell density) | 1 | 100 |
| Total volume | | 1000 |

Although the total volume is 1000 μl, 10×100 μl wells should be plated due to the viscosity of the methyl cellulose leading to a loss in the volume actually plated. In general, about 20% extra volume has to be prepared in order to achieve the desired number of wells. Thus, from a 1000 μl volume, 8 wells of 100 μl each can be plated.

Before adding the target cells, ensure that a single cell suspension has been prepared.

6. Mix the contents of the tube vigorously to obtain a homogenous master mix.

7. To ensure that as little master mix as possible remains on the walls of the tube, perform a quick spin in a centrifuge to 500 rpm. and then let the centrifuge spin down. This concentrates all the components together, but does not spin down the cells.

8. Dispense 100 μl of the reagent master mix into each of the replicate wells. This can be performed with a syringe and needle, but a repeater pipette is recommended for ease of use, reproducibility and to reduce variation.

9. Transfer the culture plate to a 37° Celsius, fully humidified incubator with an atmosphere of 5% $CO_2$. If possible, use an incubator gassed with nitrogen in order to reduce the atmospheric oxygen concentration (21%) to 5% $O_2$ since this helps increase the plating efficiency.

10. Incubate the cells for the time periods shown in Table 2 below:

TABLE 2

| SPECIES | CELL TYPE | POPULATION TESTED | INCUBATION PERIOD (days) |
| --- | --- | --- | --- |
| Mouse | Bone marrow | CFC-GEMM, BFU-E, GM-CFC, Mk-CFC | 5 |
| Rat | Bone marrow | CFC-GEMM, BFU-E, GM-CFC, Mk-CFC | 5 |
| Dog | Bone marrow | CFC-GEMM, BFU-E, GM-CFC, Mk-CFC | 5 |
| Non-human primate | Bone marrow | CFC-GEMM, BFU-E, GM-CFC, Mk-CFC | 5 |
| Human | Bone marrow | CFC-blast, CFC-GEMM, BFU-E, GM-CFC, Mk-CFC, G-CFC, M-CFC, B-CFC, T-CFC | 7–9 |
| | Peripheral blood | CFC-blast, CFC-GEMM, BFU-E, GM-CFC, Mk-CFC, G-CFC, M-CFC, B-CFC, T-CFC | 7–9 |
| | Umbilical cord blood | CFC-blast, CFC-GEMM, BFU-E, GM-CFC, Mk-CFC, G-CFC, M-CFC, B-CFC, T-CFC | 7–9 |

Step 3: Luminescence Measurement With and Without Manual Enumeration (i) Luminescence kit components: Prior to measuring luminescence, remove the ATP standard and the ATP monitoring reagent are thawed at room temperature or at 22° Celsius-23° Celsius. The ATP releasing reagent is equilibriated at room temperature or at 22° Celsius-23° Celsius.

(ii) Amounts of Luminescence Kit Components Required:

For ATP standard dose response: 4×100 μl of each dilution (4 replicates per ATP dose).

The amount of ATP releasing reagent added to each well will be 50 μl. Therefore:

Total amount of ATP releasing reagent (μl) required=50×(number of wells+24 (background and ATP wells)).

The amount of ATP luminescence-monitoring reagent added to each well will 100 μl. Therefore:

Total amount of ATP luminescence-monitoring reagent (μl) required=100×(number of wells used+24 (background and ATP wells)).

(iii) Instruments required: Luminometer. (Set luminometer parameters to: maximum integration time, 1-2 sec; initial gain (if required) at 225; shake duration (if required) to 15 s orbital; measurement temperature, 22° Celsius. If the luminometer has an injector, gain and shaking control is not necessary. 8- or 12-channel pipette.

Reagent reservoirs for an 8- or 12-channel pipette.

The performance of an ATP dose response prior to each luminescence measurement has 3 functions:
1. It tests whether the reagents are working properly.
2. It tests whether the luminometer is working correctly.
3. It allows relative luminescence units (RLU) to be converted to units of ATP, thereby standardizing the procedure so that intra- and inter-laboratory experiments can be compared.

(v) Adhesive plate covering film: To help keep the plate(s) sterile, adhesive, air permeable, sterile covering film is provided so that the part of the plate that is not being used can be covered and kept sterile until required. If using the adhesive film provided, the plate cover should be removed in a laminar air-flow hood and replaced with the film to ensure sterility.

(vi) Manual enumeration: 96-well plates suitable for use with the kits have a transparent bottom so that the contents of the wells can be viewed under an inverted microscope. Manual enumeration can be performed prior to the addition of the luminescence reagents.

Manual enumeration does not involve counting or differentiating colonies, but rather clusters of cells that comprise a "proliferation unit" or PU. A PU is a cluster of 8 or more cells that can exist individually or as part of a growing colony. Clusters can grow from the center outward producing an evenly distributed entity having a single central mass of cells. This would be considered a single PU. Alternatively, a cluster may consist of an irregular shape and be composed of one or more areas in which a concentration of cells can be seen. These areas usually appear darker than the rest of the cluster. Each of these areas is considered a PU and has to be counted. In addition, each protuberance from a developing cluster is also considered a PU. Each PU is derived from a single cell. There is a direct correlation between the number of PUs manually enumerated and the luminescence measured in Relative Luminescence Units (RLU). Little if any correlation occurs between the number of whole colonies counted (as in the case with the classical colony-forming assay) and the RLU.

Luminescence Measurement (i) ATP Standard Dose Response

Before measuring luminescence of the sample plate, an ATP standard dose response should be performed.

1. Prepare and label 5 vials (e.g. 1.5 ml volume) for the ATP dose response consisting of the following ATP concentrations: 1 µM; 0.5 µM; 0.1 µM; 50 nM and 10 nM respectively.
2. First dilution to 1 µM: Remove 100 µl of the supplied ATP solution (at 10 µM) and transfer it to vial #1. Add 900 µl of the medium provided in the kit. Mix by vortexing. This ATP concentration is 1 µM.
3. Transfer 300 µl from vial #1 to vial #2 and add 300 µl of medium. Mix. This concentration is 0.5 µM.
4. Transfer 100 µl from vial #2 to vial#4 and add 900 µl of medium. Mix. This concentration is 50 nM.
5. Transfer 100 µl from vial #1 to vial #3 and add 900 µl of medium. Mix. This concentration is 0.1 µM.
6. Transfer 100 µl from vial #3 to vial #5 and add 900 µl of medium. Mix. This concentration is 10 nM.
7. Now transfer 100 µl from vial #5 to wells E1, F1, G1, and H1 on the extra luminescence plate(s)
8. Transfer 100 µl from vial #4 to wells A2, B2, C2, and D2. (wells A1, B1, C1 and D1 do not contain ATP. These wells are for background values).
9. Transfer 100 µl from vial #3 to wells E2, F2, G2, and H2.
10. Transfer 100 µl from vial #2 to wells A3, B3, C3, and D3.
11. Transfer 100 µl from vial #1 to wells E3, F3, G3 and H3.
12. Add the required amount of ATP releasing reagent to the reservoir.
13. With an 8-channel pipette add 50 µl to the first column (A1-H1). Mix the contents by taking up the same volume in the same tips and, while dispensing and with a circular wrist action, move the pipette tips around the circumference of the well. Repeat this procedure a total of 4 times and discard tips.
14. Add 50 µl of ATP releasing reagent to each of the other columns, mixing the contents 4 times as described in Step 13. Change tips for each new addition of ATP releasing reagent.
15. Add the required amount of ATP luminescence-monitoring reagent to the second reservoir.
16. Using new tips, add 100 µl of ATP luminescence-monitoring reagent to the wells of the first column, mixing as described in Step 13 and discard tips.
17. Repeat the procedure for each new column, changing tips for each new addition of ATP luminescence-monitoring reagent.
18. Place the ATP plate in the luminometer and time 2 min before initiating measurement.

Sample Measurement

The addition of ATP releasing reagent and ATP luminescence-monitoring reagent is performed is the same manner as that for ATP.

1. Place the sample plate(s) in a humidified incubator set at 22° Celsius-23' Celsius gassed with 5% $CO_2$ for 30 mins to equilibrate.
2. If only part of the plate has been used, remove the lid under sterile conditions and attach the sterile adhesive plate cover to the empty wells to avoid any contamination. (See (iv) Adhesive Plate Covering Film above).
3. With a multichannel pipette (8- or 12-channels depending on the plate configuration), add 50 µl to the first column (A1-H1) or row (A1-12). Mix the contents by taking up the same volume in the same tips and, while dispensing, move the pipette tips around the circumference of the well. Repeat this procedure a total of 4 times. Mixing is very important.
4. Repeat this procedure of each row using new tips each time new reagent is used.
5. When ATP releasing reagent has been added to all wells, replace the plate in the incubator and leave for 15 min.
6. After 15 min, remove the plate from the incubator and, using a multichannel pipette as described in Step 3 above, and new tips, dispense 100 µl of ATP luminescence-monitoring reagent into the wells of the first column or row. Mix thoroughly as described in Step 4 and discard tips.
7. Repeat this procedure for each column or row using new tips each time ATP luminescence-monitoring reagent is dispensed.
8. When all the sample wells have been treated, transfer the plate to the luminometer and wait 2 min before luminescence measurement is initiated.

EXAMPLE 2

Measurement of the ATP Content of Incubated Hematopoietic Stem or Progenitor Cells After the incubation time has elapsed, the reagents from the ViaLight HS™ kits (Lumitech) were prepared for use. If necessary, the number of cell clusters (aggregates) or colonies that had developed in the wells of the incubated 96-well plates could be counted under an inverted microscope to ensure that a correlation between the sum, or mean, of the ratio of clusters/colonies to the relative luminescence units (RLU) was obtained (see below).

All reagents were allowed to attain room temperature before use. The ATP luminescence-monitoring reagent was reconstituted as described by the manufacturers by adding 10 ml of the supplied buffer to the lyophilized reagent and waiting 15 mins. Alternatively, 1 ml of the buffer was used to reconstitute the reagent and the latter was then aliquoted into 1.5 ml microtubes and frozen while protected from light. Aliquots were then thawed and diluted to 1 ml final volumes using the supplied buffer as needed. The ATP monitoring reagent was protected from light at all times.

The required quantity of ATP releasing reagent was transferred into the reagent trough and 100 μl aliquots were transferred, using a multi-tip pipette, to each row or column of wells of the 96-well plated previously incubated as described in Example 1 above. After dispensing the reagent to one row or column, the contents of the wells were mixed at least 4-5 times with the pipette, so that the reagents mixed well with the methyl cellulose master mixes. Addition of the reagents diluted the methyl cellulose and mixing ensured that the cells came into contact with the ATP releasing reagent. This step had to be performed in a similar manner for all wells.

Once the ATP releasing reagent had been dispensed into all of the wells containing incubated cultures, and mixed therein, the plates were typically incubated in the dark for 5 min, although the incubation could proceed for up to 30 min without loss of sensitivity.

The required amount of ATP luminescence-monitoring reagent was transferred to a new, clean trough and 20 μl of the reagent pipetted into each of the wells while ensuring that the contents of each well was mixed thoroughly. The plates were immediately transferred to a plate reader and the luminescence measured using an integration time of 1000 ms.

Measurement was given as relative luminescence units (RLU). In addition, since no two makes of luminescence readers are the same, the gain required to obtain sufficient RLU by each machine had to be empirically determined, but could also be standardized between machines as follows:

If space allowed on the same plate as the wells containing the incubated cell cultures, 100 μl of a $10^{-6}$ M standard ATP diluted in IMDM from a $10^{-5}$ M ATP stock solution was added to each of 4-6 wells. 100 μl of ATP releasing agent was then added and incubated for the same period as had been used for the cell culture wells. 20 μl of ATP monitoring reagent was then added and the plate transferred to the plate reader and the luminescence measured at an integration time of 1000 ms. The gain was adjusted such that the luminescence from the ATP standard was approximately 20,000 RLU. By adjusting the gain of the machine to obtain this number of RLU, and then reading the remaining wells of the plate (containing the incubated cells), no overflow values occurred, thereby obviating the need for a second or multiple reading. In all cases, the luminescence was measured in the shortest possible time period possible, because the luminescence decreased rapidly with time.

Counting colonies in the traditional manner, i.e. after the normal incubation time and when the colonies were mature, does not correlate with luminescence because the luminescence assay measures cell proliferation and in mature colonies, cell proliferation has almost ceased. It was therefore necessary to define the time point or range during culture at which cell proliferation was greatest.

The correlation between the initial plated cell concentration (0.25, 0.5, 0.75, 1, 1.5, $2 \times 10^5$/well) and the mean (FIGS. 1A, 2A, 3A and 4A respectively) or sum (FIGS. 1B, 2B, 3B, and 4B respectively) of relative luminescence units (RLU) measured at 4 days (FIGS. 1A and 1B), 7 days (FIGS. 2A and 2B), 10 days (FIGS. 3A and 3B) and 14 days (FIGS. 4A and 4B) after culture initiation, as a function of the integration time and/or gain of the plate reader. In FIGS. 1A-4B the value 2000 represents an integration time of 2000 ms. "Max" represents the maximum integration time. The values 200, 215, 225 or 250 represent the gains that were used with the respective integration times.

Growing cell cultures were terminated every day over a 10-13 day period. Before measuring luminescence, the plates were manually counted. During the earliest phase of growth no colonies are formed. However, clusters of cells could be seen, representing proliferating cell aggregates, denoted as "proliferative units" (PU), arbitrarily defined as a cluster of 8 or more cells. However, with time, PUs become colonies and in many cases PUs can be identified within colonies. These areas exhibit a high accumulation of cells or areas within a colony that allowed the colony to grow from a completely round ball of cells into an irregular form. The areas of irregularity were therefore considered PUs and were counted.

Figure 5:
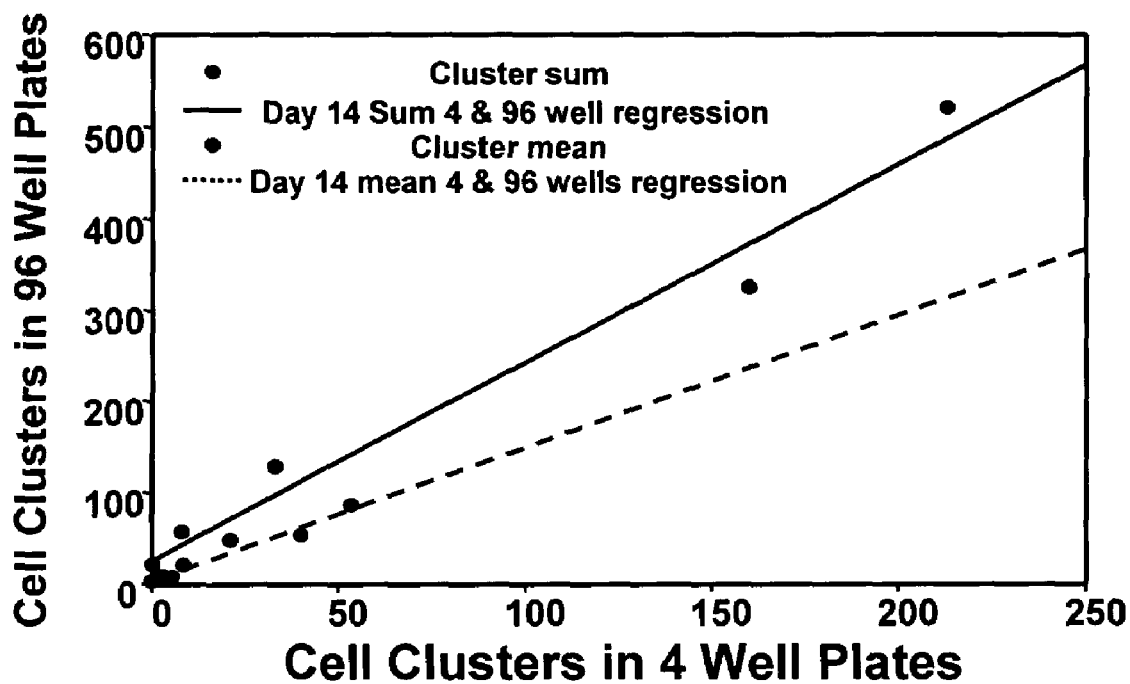
FIG. 5 shows a direct correlation between clusters counted manually in a conventional quadruplicate assay format and the 96-well plate format of the HALO method
Figure 6:
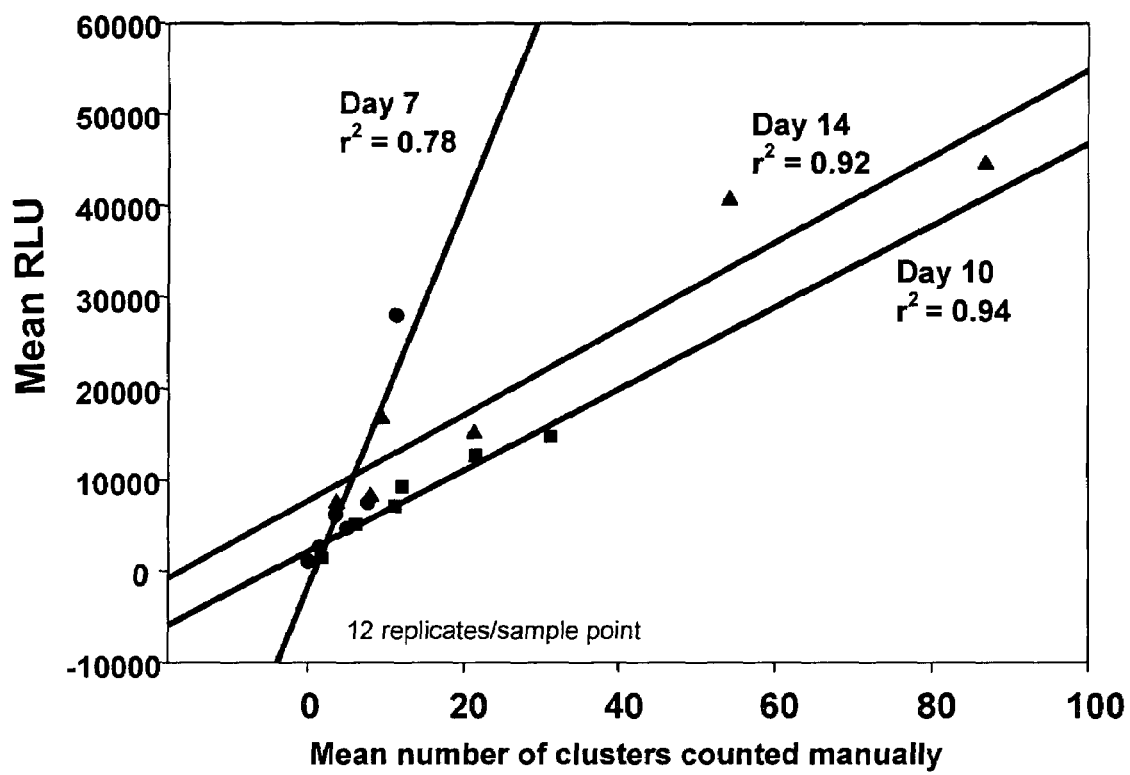
FIG. 6 shows the correlation on days 7, 10 and 14 between the mean number of cluster counts of erythroid bursts and the mean luminescence (RLU).

FIG. 5 shows a direct correlation between clusters counted manually in a conventional quadruplicate assay format and the 96-well plate format of the HALO method derived from peripheral blood erythropoietic progenitor cells (burst-forming units-erythroid, BFU-E). FIG. 6 shows the correlation on days 7, 10 and 14 between the mean number of cluster counts of erythroid bursts and the mean luminescence (RLU). Although there are very low numbers of BFU-E clusters on day 7, the slope of the curve is steep because of the high cell proliferation occurring at this time.

EXAMPLE 3

Hematopoietic Stem and Progenitor Cell Lines and Their Associated Cytokine Effectors Hematopoietic stem and progenitor cells are induced to differentiate into hematopoietic cell subpopulations by exposure to one or more growth factors/cytokines, as shown in Table 3 below.

TABLE 3

| Development stage | Lineage | Population name | Population abbreviation | Stimulatory Growth factors and cytokines |
|---|---|---|---|---|
| Stem cell (Most primitive in vitro stem cell) | None | Long-term culture-initiating cells | LTC-IC | Stimulated by microenvironmental cells |

TABLE 3-continued

| Development stage | Lineage | Population name | Population abbreviation | Stimulatory Growth factors and cytokines |
|---|---|---|---|---|
| Stem cell (Very primitive in vitro stem cell) | None | Colony-forming cell-Blast | CFC-Blast | Flt3L, SCF and IL-6 |
| Stem cell (Primitive in vitro stem cell) | None | High proliferative potential colony-forming cell | HPP-CFC | IL-1, IL-3, IL-6, SCF, M-CSF |
| Stem cell (Most mature in vitro stem cell) | None | Colony-forming cell granulocyte, erythroid macrophage, megakaryocyte | CFC-GEMM | IL-3, IL-6, GM-CFC, G-CSF, EPO, and SCF and/or Flt3L |
| Progenitor | Erythroid | Burst-forming unit-Erythroid | BFU-E | EPO<br>IL-3 and EPO<br>SCF and EPO<br>IL-3, SCF and EPO |
| Progenitor | Granulocyte-Macrophage | Granulocyte-macrophage colony-forming unit | GM-CFC | GM-CSF<br>IL-3 and GM-CSF<br>IL-3, SCF and GM-CSF |
| Progenitor | Megakaryocyte | Megakaryocyte colony-forming cell | Mk-CFC | TPO<br>IL-3, IL-6 and TPO |
| Progenitor | T lymphocyte | T cell colony-forming cell | T-CFC | IL-2<br>IL-7, Flt3L and IL-15 |
| Progenitor | B lymphocyte | B cell colony-forming cell | B-CFC | IL-7<br>IL-7 and Flt3L |
| Precursor | Erythroid | Colony-forming cell-erythroid | CFU-E | EPO |
| Precursor | Myeloid-Neutrophil | Granulocyte colony-forming cell | G-CFC | G-CSF<br>GM-CSF, high concentrations |
| Precursor | Myeloid-Basophil | Colony-forming cell-basophil | CFC-Bas | IL-3<br>IL-3 and SCF |
| Precursor | Myeloid-Eosinophil | Colony-forming cells-eosinophil | CFC-Eo | GM-CSF and IL-5 and IL-3 |
| Precursor | Macrophage | Macrophage colony-forming cell | M-CFC | M-CSF<br>M-CSF, GM-CSF, IL-3<br>GM-CSF, low concentrations |

EXAMPLE 4

Figure 7:
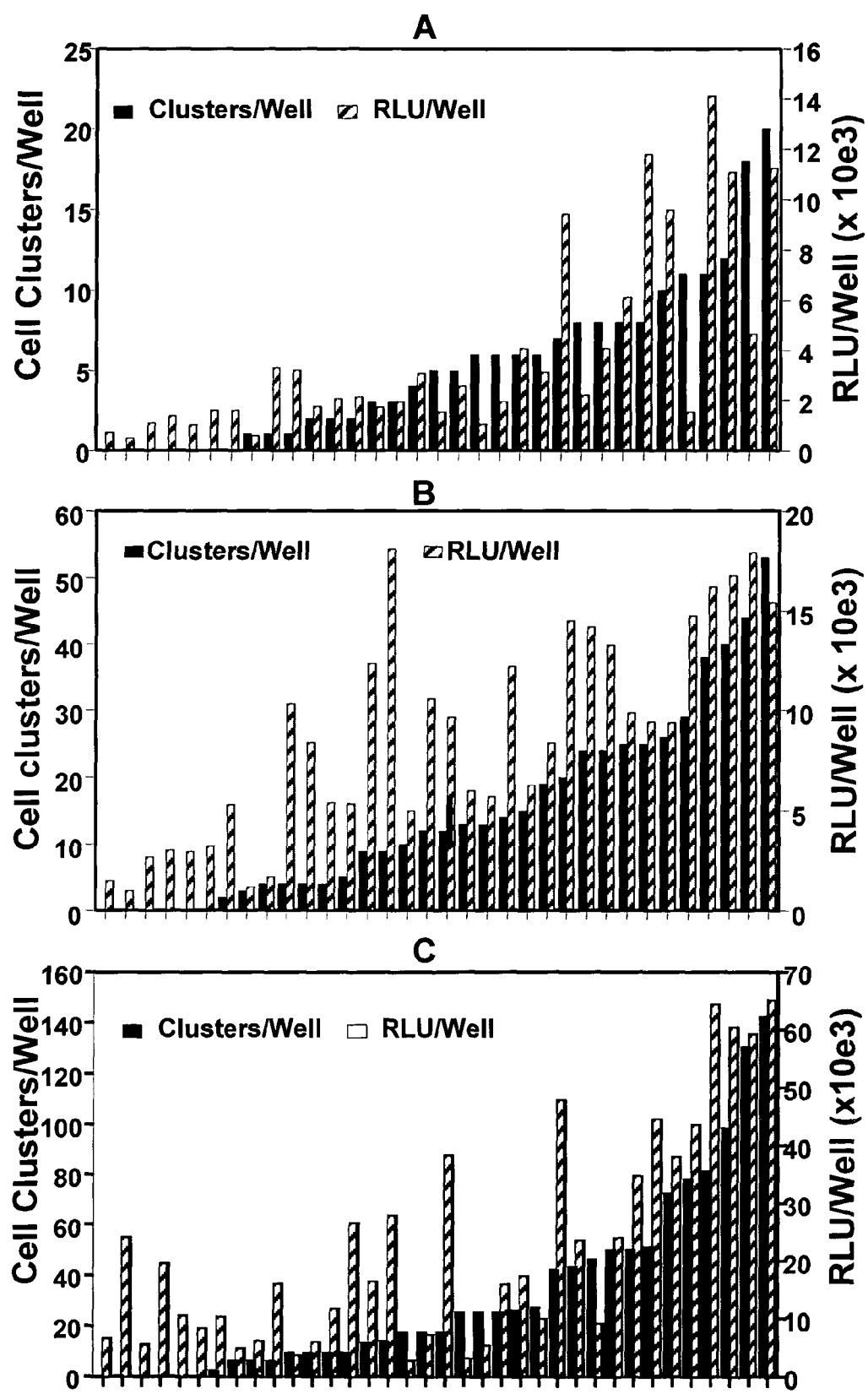
FIGS. 7A-7C illustrate histograms showing the number of cell clusters counted manually per well and the relative luminescence units (RLU) per well at day 7 (FIG. 7A), day 10 (FIG. 7B) and day 14 (FIG. 7C) of incubation.

Proliferation of Hematopoietic Stem and Progenitor Cells Measured by Colony Counting and ATP Determination When cell proliferation was measured as a function of time in culture, some aggregates or colonies contained cells that were proliferating, while others were not, as shown in FIGS. 7A-7C. Wells, therefore, could contain few colonies, but still exhibit high cell proliferation. The results shown in FIGS. 7A-7C show that the number of cell clusters counted per well does not correlate with the cell proliferation as detected using the luminescence of the present invention.

In contrast, in those wells in which minimal or no cluster formation was detected, luminescence could be detected. In some wells, the luminescence was significantly greater than expected from the number of cell clusters counted, indicating that cell proliferation was occurring and that the proliferating cells, were primitive because of their increased proliferative capacity. On day 10, most wells contained cells that were proliferating. By day 14, this proliferative capacity was only seen in some wells, indicating that proliferation has ceased (RLU lower than the cell cluster count) or is declining. Those wells exhibiting a significantly greater RLU than determined by manual cell cluster counting showed that cells were present that were capable of extensive proliferation and were probably stem cells.

Figure 8:
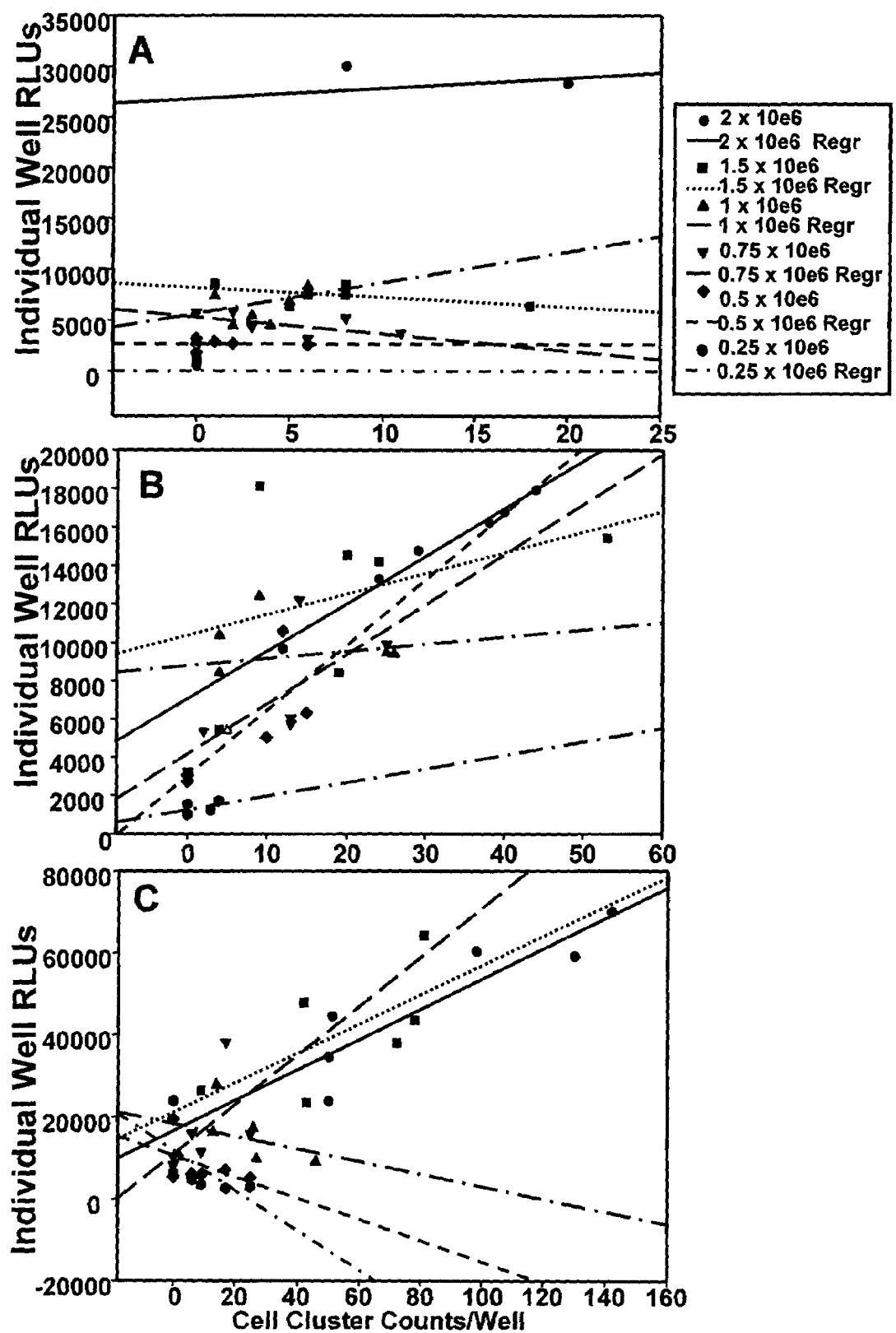
FIGS. 8A-8C illustrate the lack of correlation between cell cluster counts per well and the relative luminescence units (RLU) per well on day 7 (FIG. 8A), day 10 (FIG. 8B) and day 14 (FIG. 8C) of culture incubation.

Little or no correlation existed between the number of individual colonies and the luminescence, as shown in FIGS. 8A-8C. However, under the typical incubation and culture conditions of the assay of the present invention, a well containing a few colonies, but with high indicated cell proliferation, showed that the cells in the culture have high proliferative capacity. In other words, the cells were primitive in nature.

Figure 9A:
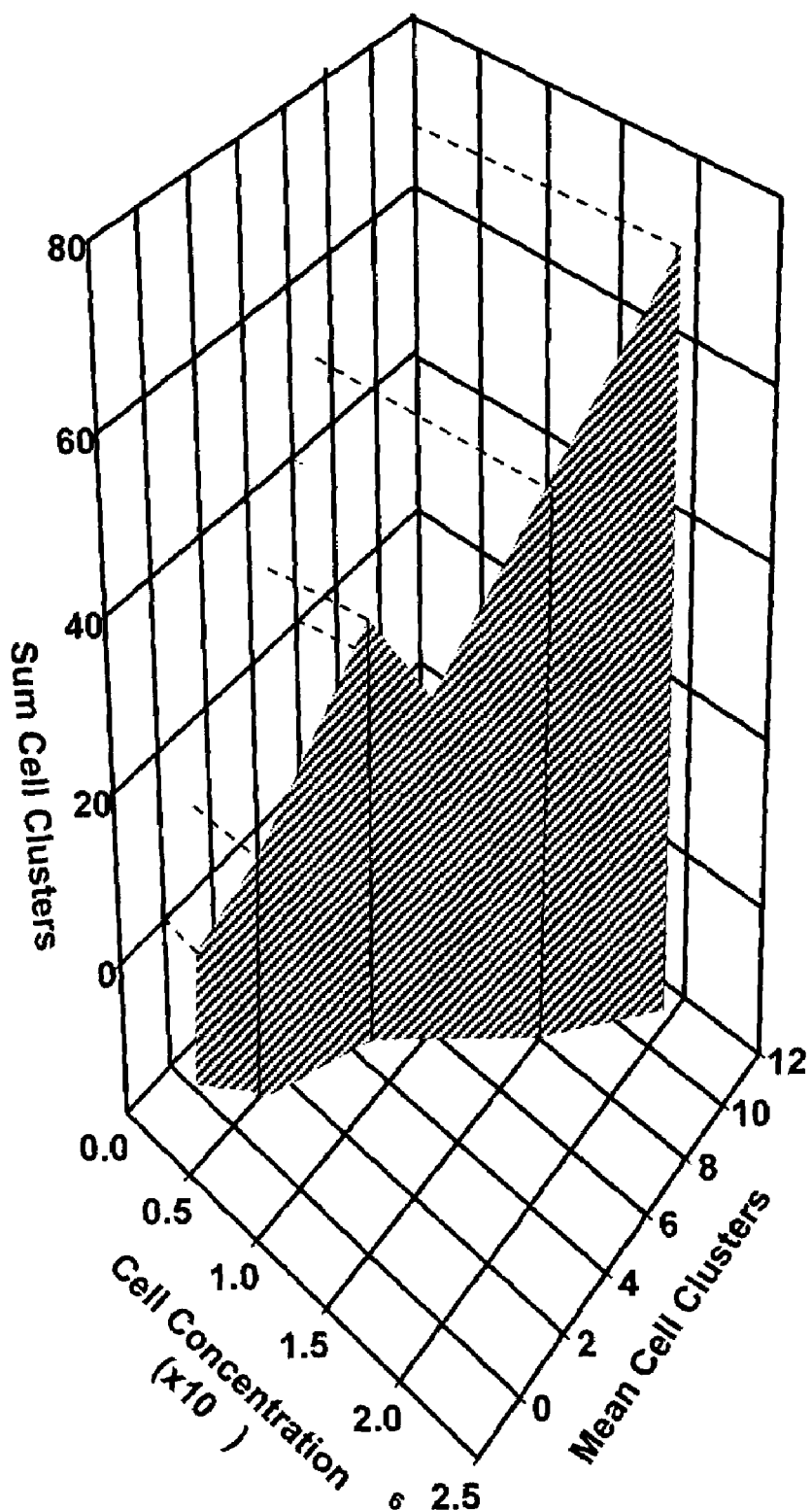
FIGS. 9A-9C show the correlation between the sum, or mean, of the cell cluster counts with the sum or mean of the relative luminescence units (RLU) measured on day 7 (FIG. 9A), day 10 (FIG. 9B) and day 14 (FIG. 9C) of culture incubation.
Figure 9B:
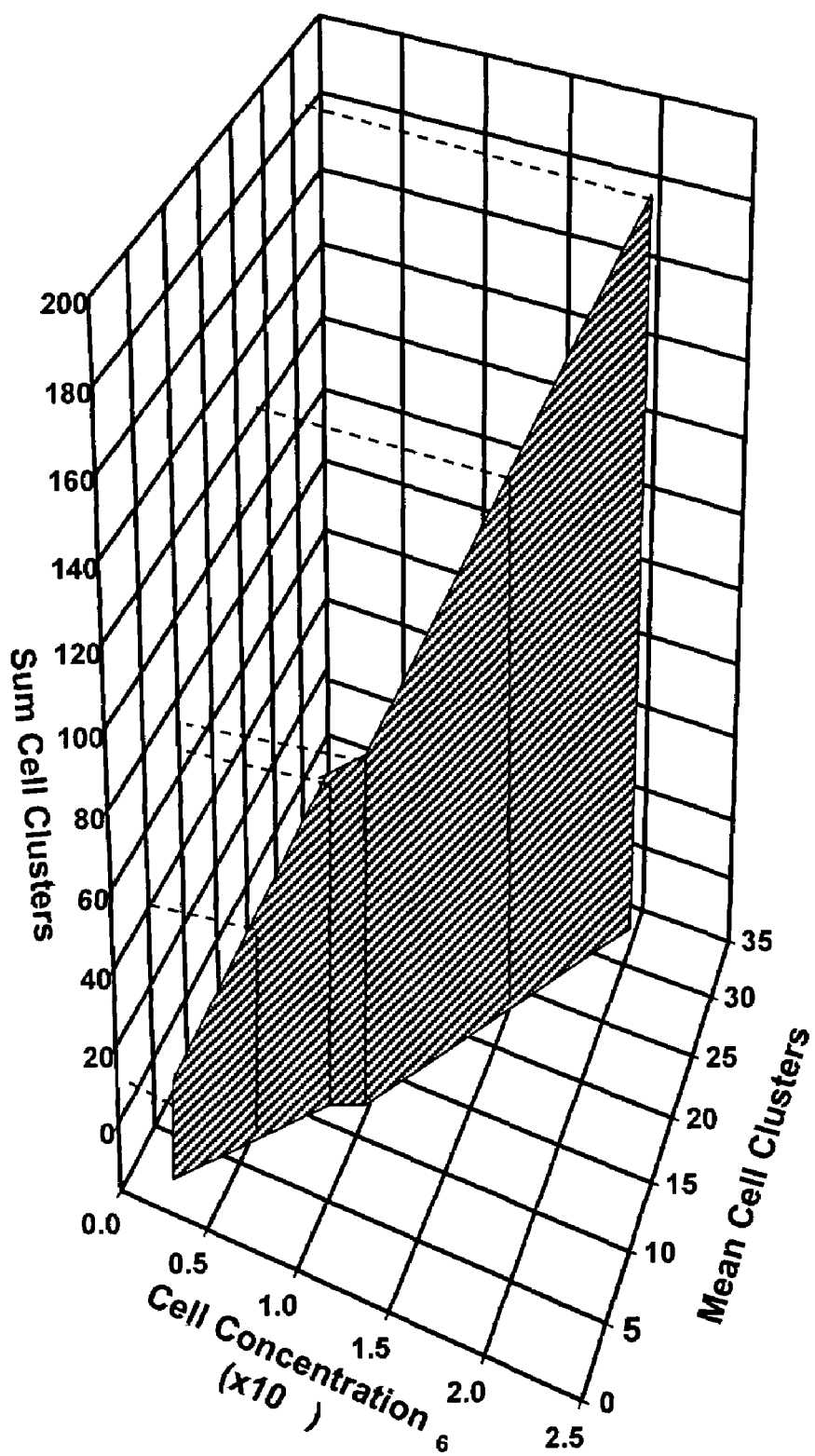
Figure 9C:
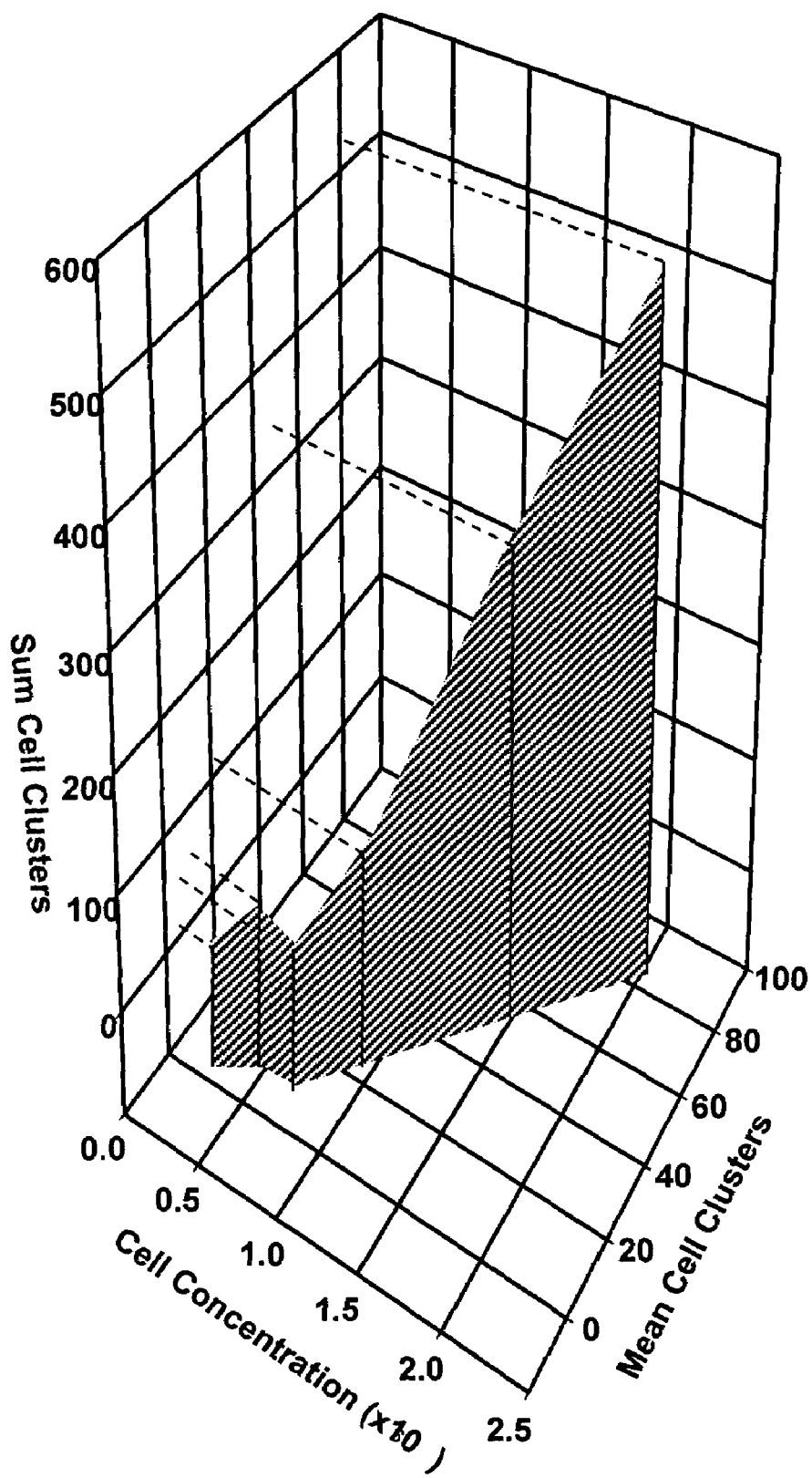

The number of colonies in a well did not generally correlate with the RLU from that well, as shown in FIGS. 8A-8C. In contrast, however, in the high-throughput assay method of the present invention, the luminescence measurements were made over the whole area of each and every replicate well, and not from the individual cell aggregates or colonies within these areas. The sum of the luminescent values of aggregates or colonies, or the mean of the aggregates or colonies from all replicate wells, can be predicted to correlate with the sum or mean of the luminescence emitted from the replicate wells, as shown in FIGS. 9A-9C.

Figure 10:
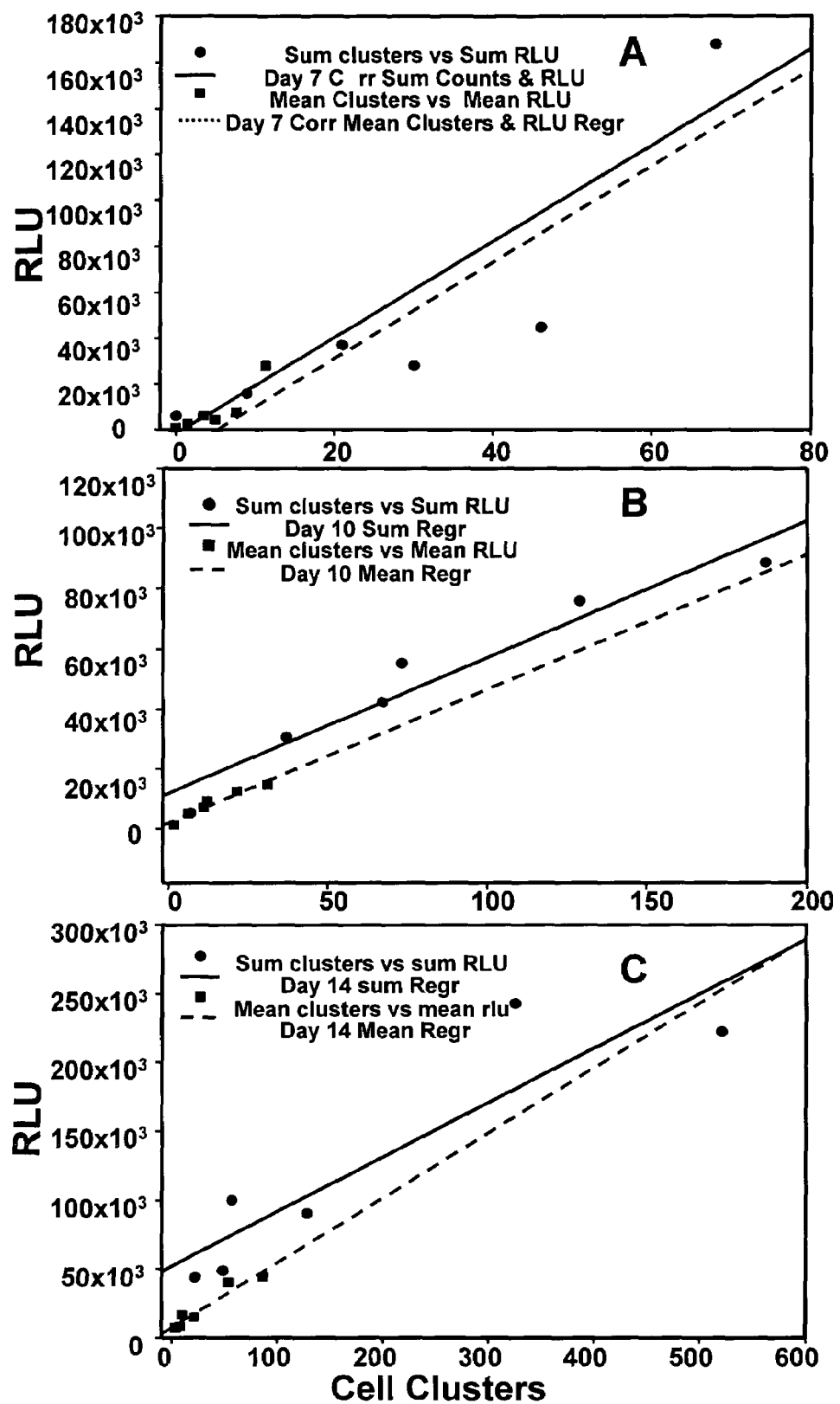
FIGS. 10A-10C show the correlation between cell concentration, sum of the replicate cell clusters and mean of the replicate cell clusters on day 7 (FIG. 10A), day 10 (FIG. 10B) and day 14 (FIG. 10C) of culture incubation.

There was a direct correlation between the sum, or mean, of all the cell aggregates or colonies from all replicate wells and the sum or mean of the RLU from all replicate wells. Furthermore, this relationship was cell dose dependent, as illustrated in FIGS. 10A-10C.

These results, as opposed to those in FIGS. 8A-8C indicate that using the sum or the mean of the replicates from particular sample, in this case, replicates at different cell concentrations, a direct correlation exists between the 3 parameters. If measurement of luminescence is depicted as the sum or the mean of the replicates, there was also be a direct correlation with the sum and/or mean of the cell clusters, as shown in FIGS. 10A-10D.

Figure 11:
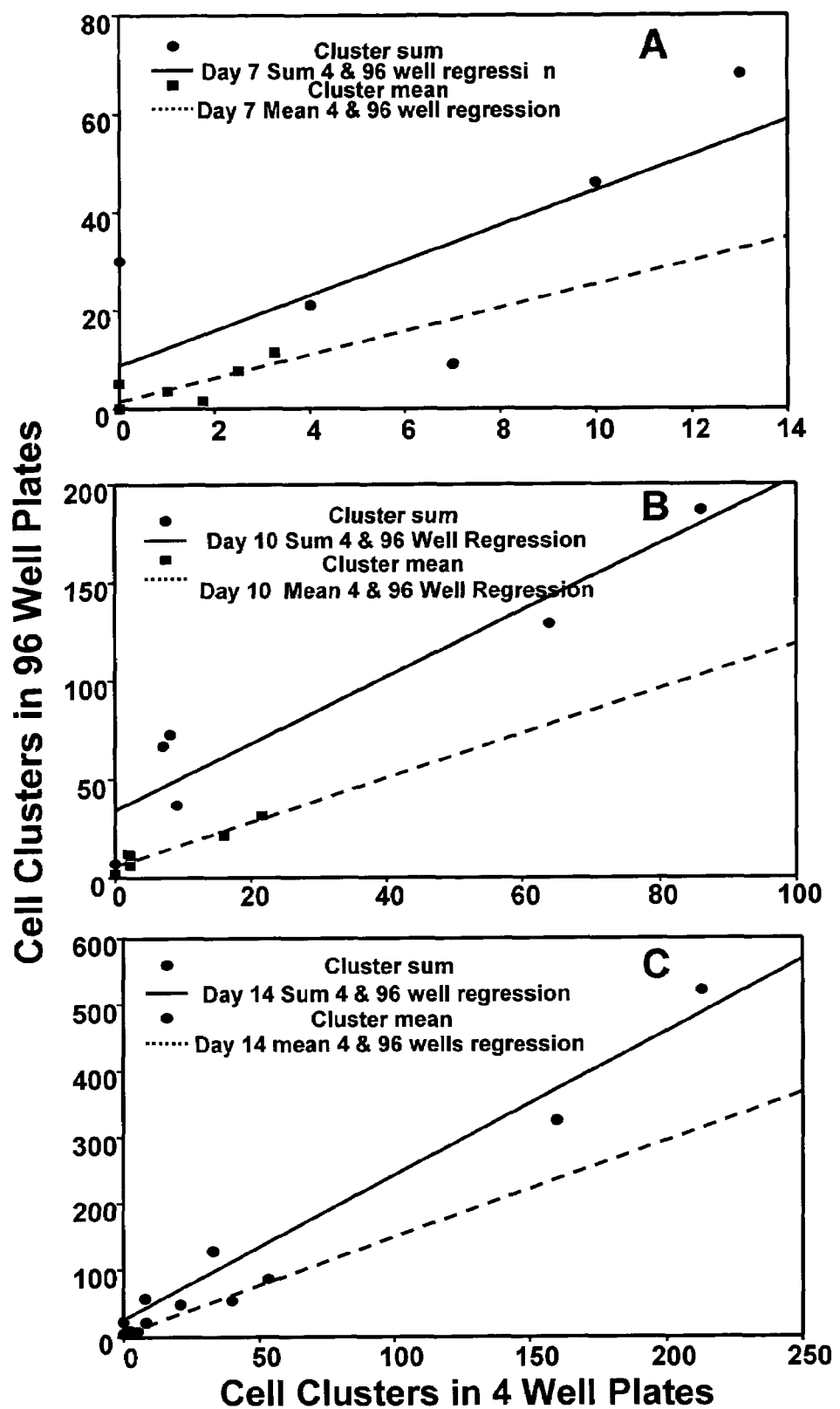
FIGS. 11A-11C show the correlation between a manual 4-well assay and the 96-well assay method of the present invention. The results were plotted as either the sum or mean of the replicates obtained on day 7 (FIG. 11A), day 10 (FIG. 11B) and day 14 (FIG. 11C) of culture.

To validate the 96-well plate assay, experiments using both assay systems were performed in parallel. A direct correlation exists between the 4-well and the 96-well plate assay, as shown in FIGS. 11A-11C and indicates that the results obtained from the latter have been validated.

EXAMPLE 5

Use of High-throughput Stem/Progenitor Cell Assays to Determine the Ability of a Test Compound to Modulate the Proliferation of Hematopoietic Stem and Progenitor Cells The HT-SPCA of the present invention is used to test dose responses for a variety of compounds that can interact with hematopoietic stem and progenitor cells. The agents either stimulate or inhibit and/or kill hematopoietic cells. Increasing doses of an agent can stimulate cells, but then be inhibitory by being toxic and causing necrosis. Other agents can be toxic at high doses, but induce apoptosis at lower concentrations.

Agents with known action on hematopoietic stem and progenitor cells include, 5-fluorouracil (5-FU), hydroxyurea, cytosine arabinoside (ara-C). busulphan, 3'azido-3'deoxythymide (AZT), cycloheximide, actinomycin D, etoposide, BCNU, doxorubicin, cisplatin (low hemotoxicity) and carboplatin. Growth factors known to inhibit the proliferation of stem and progenitor cells such as interferon-γ (IFNγ), tumor necrosis factor-α (TNF-α) and transforming growth factory-β(TGFβ) are also tested. Neutraceuticals include, for example, the anti-inflammatory phytochemicals, black and green tea polyphenols, resveritrol, limonene and curcumin.

For these and other agents to be tested, mononuclear cells derived from peripheral blood, bone marrow and cord blood are used. CD34+ cells derived from these tissues can also be used. HT-SPCA assays for CFU-GEMM, GM-CFC, BFU-E, Mk-CFC and CFU-E, CFC-blast, HPP-CFC, M-CFC and G-CFC induced to proliferate and differentiate by contacting the cell populations with the appropriate cytokine of combinations of cytokines as given in Example 3, Table 1, above, are also performed.

HT-SPCA can be used to detect and predict hemotoxicity against hematopoietic stem and progenitor cell populations. To validate the inhibition/hemotoxicity of the agents, both manual CFA and the HT-SPCA are performed in parallel. One of the end points is to determine the IC50 and IC90 for the drug.

EXAMPLE 7

Measurement of Oxidative Damage

Oxidative damage is indicated in a wide range of pathological conditions such as carcinogenesis, diseases associated with inflammation and ischemia-reperfusion injury as well as in normal metabolic activity. Xenobiotics, environmental toxins and radiation induce damage by generating free radicals and reactive oxygen species (ROS) that can lead to mutation and cancer. The routine measurement of oxidative damage to hematopoietic cells, let alone for hemotoxicity testing, has never been attempted.

The assay system developed for the HALO methods of the present invention provides a procedure to measure oxidative stress and DNA damage based on that developed for flow cytometry. Stem and multilineage progenitor cell assays are staged in exactly the same manner as for HALO. After an incubation period of 5-10 days, 250 μl of PBS are be added to the wells, the contents mixed and the plates centrifuged at 300 g for 10 min at room temperature. Fluid (300 μl) will be aspirated from each well using a well plate washer. Thereafter, 200 μl of ice-cold Optilyse Reagent (Beckman Coulter) containing a final concentration of 0.01% Triton X-100 is added, the contents of the wells mixed and the plates incubated at 4° Celsius for 10 mins. The presence of Triton X-100 is to permeabilize the cells. Optilyse reagent is a combination cell fixative and lysis reagent for erythrocytes. The plates are centrifuged again, the fluid aspirated and 100 μl of OxyDNA reagent added and incubated for 20 mins at 37° Celsius. Fluorescence is then measured in a plate reader by excitation at 455 nm and emission at 530 nm (for FITC) or 590 nm (for Texas Red).

EXAMPLE 8

HALO Multilineage Testing Platform.

Figure 12A:
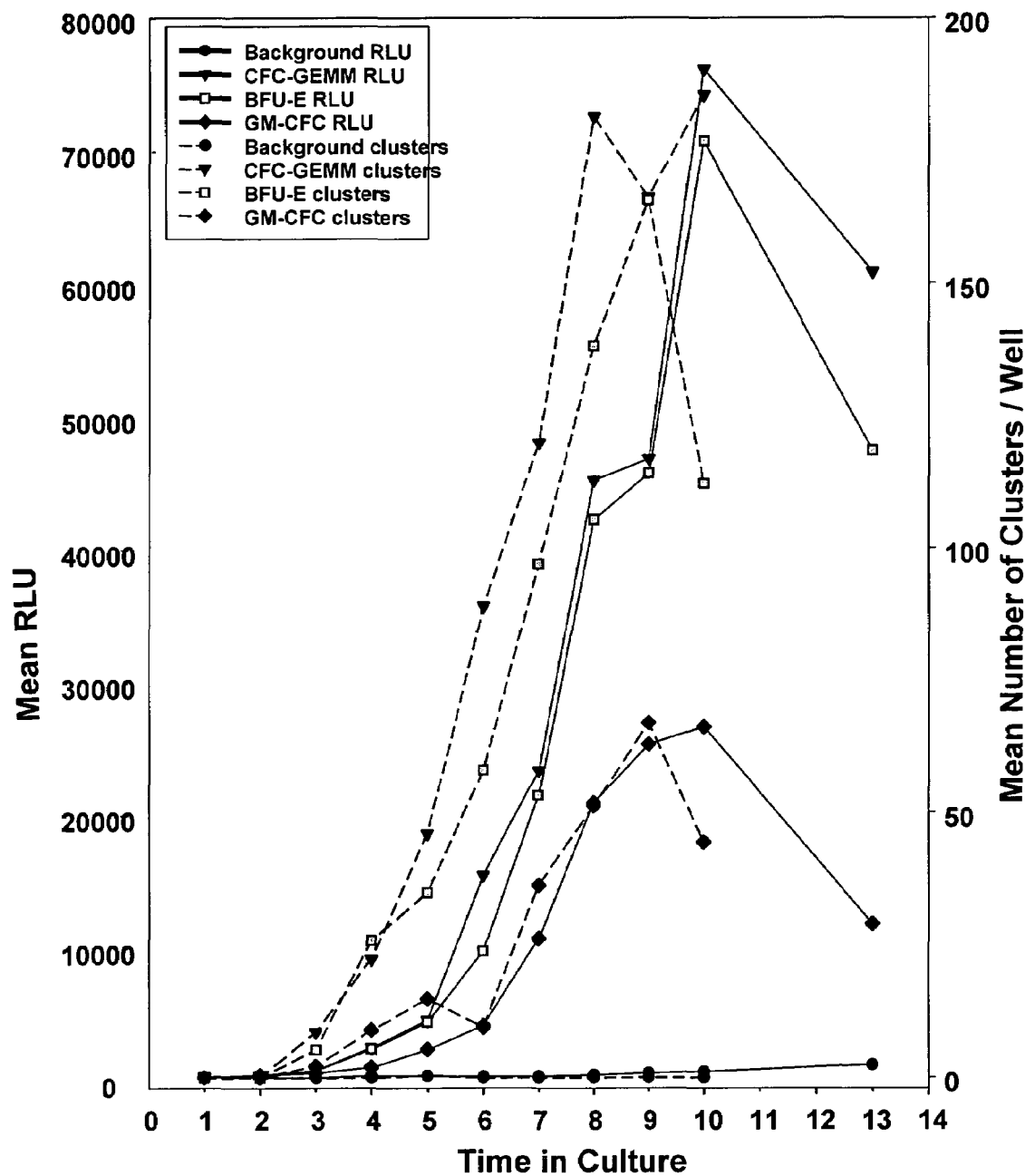
FIGS. 12A and 12B show a comparison between manual cluster counts and luminescence using human bone marrow mononuclear cells.
Figure 12B:
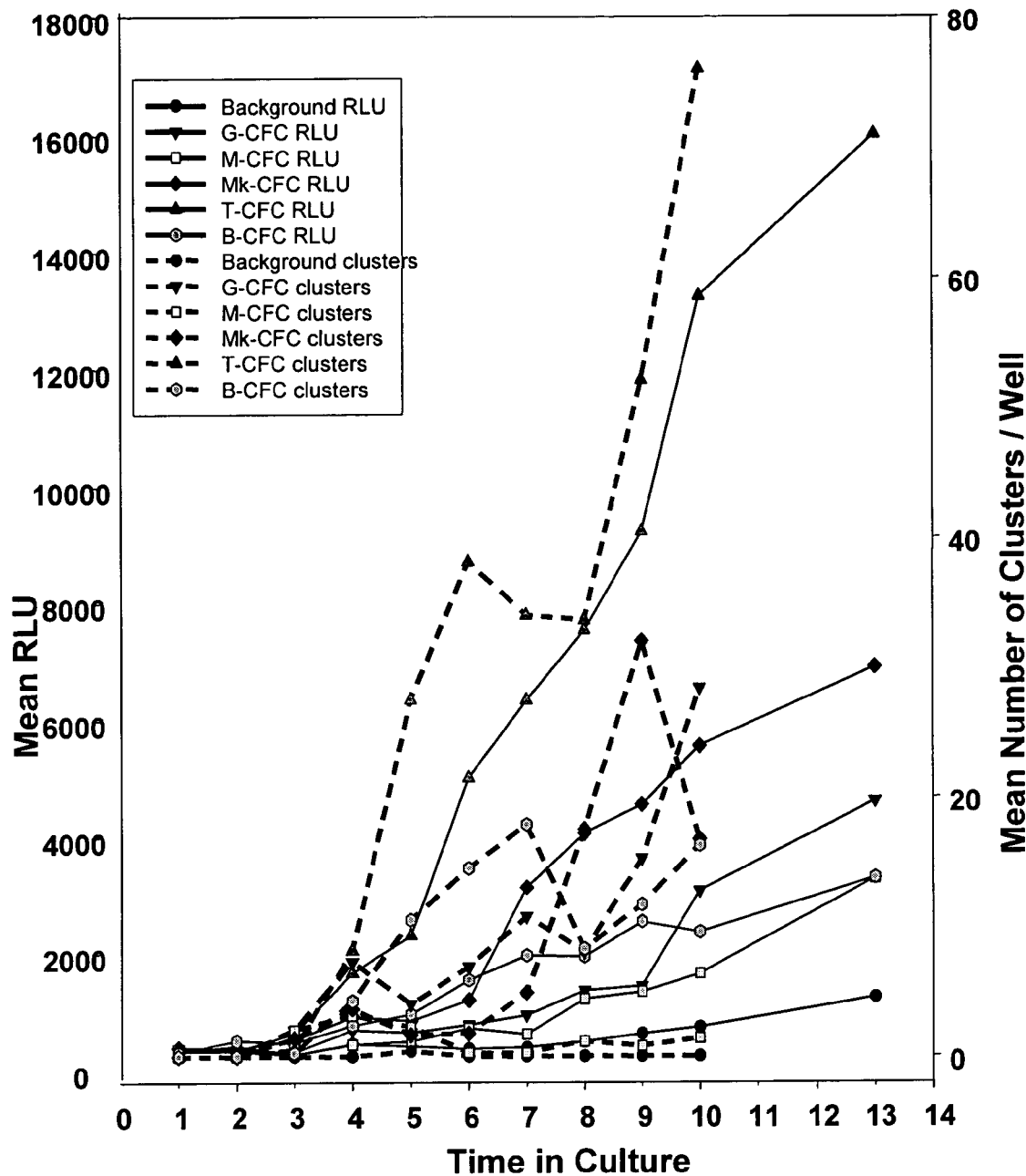

The three stem cell populations to be tested were the colony-forming cell-blast (CFC-blast), the high proliferative potential colony-forming cells (HPP-CFC) and the colony-forming cell- granulocyte, erythroid, macrophage, megakaryocyte (CFC-GEMM). The HALO platform of the present invention can be used to detect colony-forming cells of the erythropoietic progenitor (BFU-E) and precursor (CFU-E) cells, granulocyte-macrophage progenitor (GM-CFC) and granulocyte (G-CFC) and macrophage (M-CFC) precursor cells, megakaryocyte progenitor cells (Mk-CFC) and T- and B-lymphocyte progenitor cells (T-CFC and B-CFC). FIGS. 12A and 12B show a comparison between manual cluster counts and luminescence using bone marrow mononuclear cells (BMMNC) as targets cultured in 5% FBS and 20% serum supplements as a function of time. The background remains extremely low throughout the study period. T- and B-cell colony formation can also be detected. This can be substantially increased if T-lymphocytes are activated with phytohemaglutin (PHA) and B-lymphocytes are stimulated with pokeweed mitogens (PWM). Cluster counts can parallel the luminescence measurements and, therefore, clusters represent the "proliferative units" being measured by the luminescence read-out.

EXAMPLE 9

HALO as a Multispecies Platform

Figure 13:
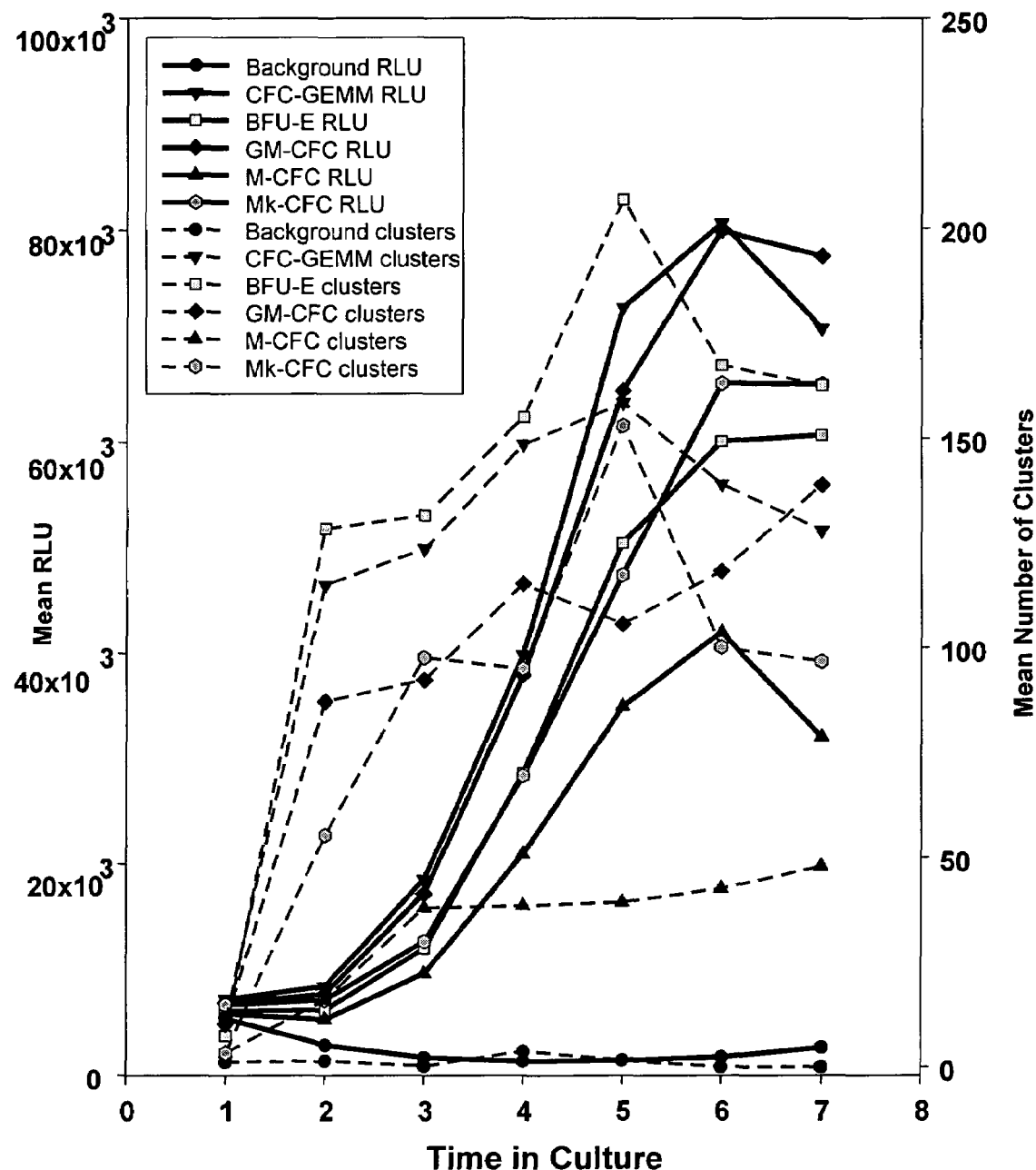
FIG. 13 shows a comparison between manual cluster counts and luminescence using mouse bone marrow mononuclear cells.
Figure 14:
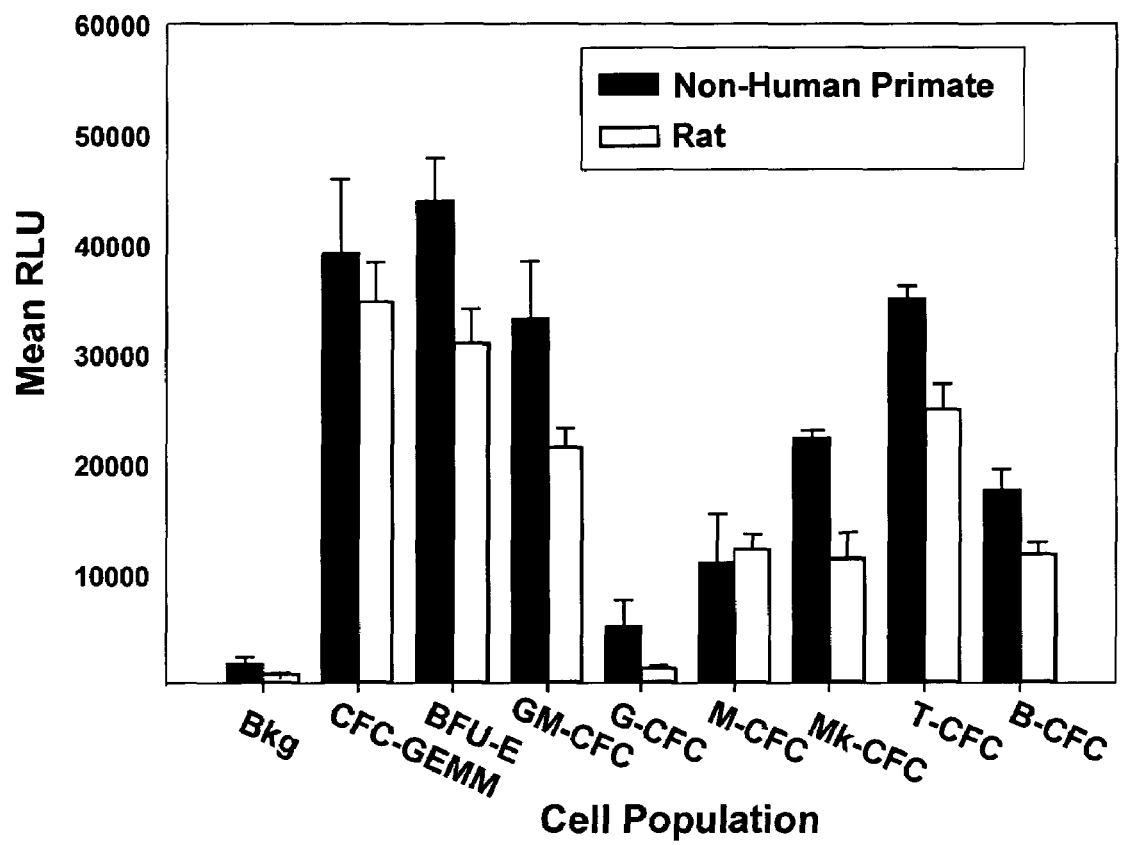
FIG. 14 shows stem and multilineage cell assays using frozen non-human primate and rat bone marrow as targets.

HALO can be used not only to study virtually all lympho-hematopoietic colony-forming cell populations from human target tissue (peripheral blood, bone marrow and cord blood), but also those from different animal species (non-human primate, dog, rat and mouse). FIG. 13 shows the response of mouse bone marrow cells with time performed simultaneously with the human study depicted in FIGS. 12A and 12B. FIG. 14 shows stem and multilineage cell assays using frozen non-human primate and rat bone marrow as targets.

EXAMPLE 10

Verification of Cell Lineage Markers

To verify that the lineages being detected by HALO contain appropriate lineage-specific cells, human bone marrow cells grown under the same lineage-specific conditions used for the HALO technique were immunophenotyped. The following cell populations/lineages have been analyzed by HALO: Multipotential stem cells (CFC-GEMM) stimulated with EPO, GM-CSF, G-CSF, IL-3, IL-6 and SCF; Erythropoietic progenitor cells (BFU-E) stimulated with EPO, IL-3 and SCF; Erythroid precursor cells (CFU-E) stimulated with EPO alone; Granulocyte-macrophage progenitor cells (GM-CFC) stimulated with GM-CSF, IL-3 and SCF, and granulocyte (G-CFC) and macrophage (M-CFC) precursor cells stimulated with G-CSF and M-CSF respectively; megakaryocyte progenitor cells (Mk-CFC) stimulated with TPO, IL-3 and IL-6; T-lymphocytes (T-CFC) stimulated with IL-2 or IL-2 and PHA; B-lymphocytes (B-CFC) stimulated with IL-7 alone or IL-7 and PWM. The CFC-blast population is stimulated with either IL-3 and IL-6 or IL-3 and SCF while the HPP-CFC stem cell population requires the same growth factor combination as CFC-GEMM, but with the addition of IL-1 and M-CSF. Eosinophil precursor cells are stimulated with IL-3, interleukin-5 (IL-S) and GM-CSF, and Baso-CFC are stimulated with IL-3 alone. A particular advantage of the methods of the present invention in the field of immunotherapy, is the ability to grow and detect macrophage-derived and lymphocyte-derived dendritic cells.

Multipotential stem cells were stimulated with EPO, granulocyte-macrophage colony-stimulating factor (GM-CSF), granulocyte colony-stimulating factor (G-CSF), IL-3 and SCF; BFU-E were stimulated with EPO, IL-3 and SCF; GM-CFC were stimulated with GM-CSF, IL-3 and SCF, while M-CFC were stimulated with macrophage colony-stimulating factor (M-CSF). Mk-CFC were stimulated with thrombopoietin (TPO), IL-3 and interleukin-6 (IL-6), while T-CFC were stimulated with interleukin-2 (IL-2) and phytohemaglutinin (PHA) and B-CFC were stimulated with interleukin-7 (IL-7) and pokeweed mitogens (PWM).

After 12 days, methyl cellulose-containing cultures were diluted by the addition of PBS, and cells were transferred to 5 ml tubes, and harvested by centrifugation. After discarding the supernatants, cells were resuspended in 500 µl of phosphate buffered saline (PBS), and 100 µl aliquots analyzed by flow cytometry. All cells were analyzed by gating through the pan-leukocyte CD45 marker, that is, CD45 was common to all flow cytometry panels. The results in Table 1 below show the absolute cell concentration (µl/sample) exhibiting a specific membrane marker and the percentage of cells expressing this marker. These results show that cells are present that have not been identified by a specific marker. Nevertheless, it is clear that those cells that should be present, are present. The concentrations and combinations of growth factors used are typical of those employed by other laboratories.

TABLE 4

Phenotypic Analysis of Cells taken from HALO Cultures on Day 13
(Cells/µl sample gated through CD45/Percentage of total cells gated through CD45)

| Marker | CFC-GEMM | BFU-E | GM-CFC | M-CFC |
|---|---|---|---|---|
| CD34 | 11/0.05% | 9/0.06% | 8/0.08% | — |
| CD117 | 345/2.55% | — | — | — |
| CD133 | 439/3.24% | — | — | — |
| Glycophorin | 3183/25% | 7437/54% | — | — |
| CD14 | 1509/9.3% | 669/3.9% | 1726/16.8% | — |
| CD15 | 256/1.6% | 194/1.1% | 109/1.1% | 289/17.8% |
| CD41/61 | 1266/9.2% | 1358/8.5% | — | — |
| CD3 | — | — | — | — |
| CD3/CD4 | — | — | — | — |
| CD3/CD8 | — | — | — | — |
| CD3/CD56 | — | — | — | — |
| CD19 | — | — | — | — |

| Marker | Mk-CFC | T-CFC | B-CFC |
|---|---|---|---|
| CD34 | 4/0.1% | — | — |
| CD117 | — | — | — |
| CD133 | — | — | — |
| Glycophorin | — | — | — |
| CD14 | 409/9.7% | — | — |
| CD15 | 44/1.1% | — | — |
| CD41/61 | 2227/48.1% | — | — |
| CD3 | — | 785/31.4% | — |
| CD3/CD4 | — | 447/17.9% | — |
| CD3/CD8 | — | 291/11.6% | — |
| CD3/CD56 | — | 180/7.0% | — |
| CD19 | — | — | 714/21.9% |

EXAMPLE 11

HALO Multitasking Capability-measurement of Cell Proliferation and Apoptosis in the Same Assay Fresh human PBMNCs were cultured under BFU-E-stimulating conditions, together with 3 concentrations of DOX, namely 1 ng/ml (low), 10 ng/ml (medium) and 100 ng/ml (high) as per a typical HALO test procedure. Replicate plates were used so that the effects of DOX could be examined at 2 time points, namely days 3 and 7. At each time point, using the APOGLOW™ detection kit (Cambrex Bio-Science), ATP releasing reagent and ATP luminescence-monitoring reagent were added and the luminescence read immediately. A second luminescence reading was taken when the nadir ATP value occurred. At this point an ADP converting reagent (ADP-CR) was then added, which converts ADP to ATP and the luminescence measured when the conversion reached a plateau. From these 3 measurements, the ADP:ATP ratio was determined. FIGS. 15A and 15B show the mean RLU values for each of the DOX concentrations measured at the 2 time points. Whereas there is little or no effect of the lowest DOX concentration, both the medium and highest concentrations can be seen to decrease the luminescence indicating a reduction in growth potential of the treated cells. The effect on the ADP:ATP ratios are shown in FIGS. 16A and 16B. On day 3, the increase in ADP:ATP ratio is due to apoptosis of cells with low proliferative capacity. On day 7, BFU-E and immediate progeny are proliferating rapidly and are being induced into apoptosis by the presence of DOX.

EXAMPLE 12

Measurement of Cell Proliferation and Apoptosis in One Procedure

Figure 15:
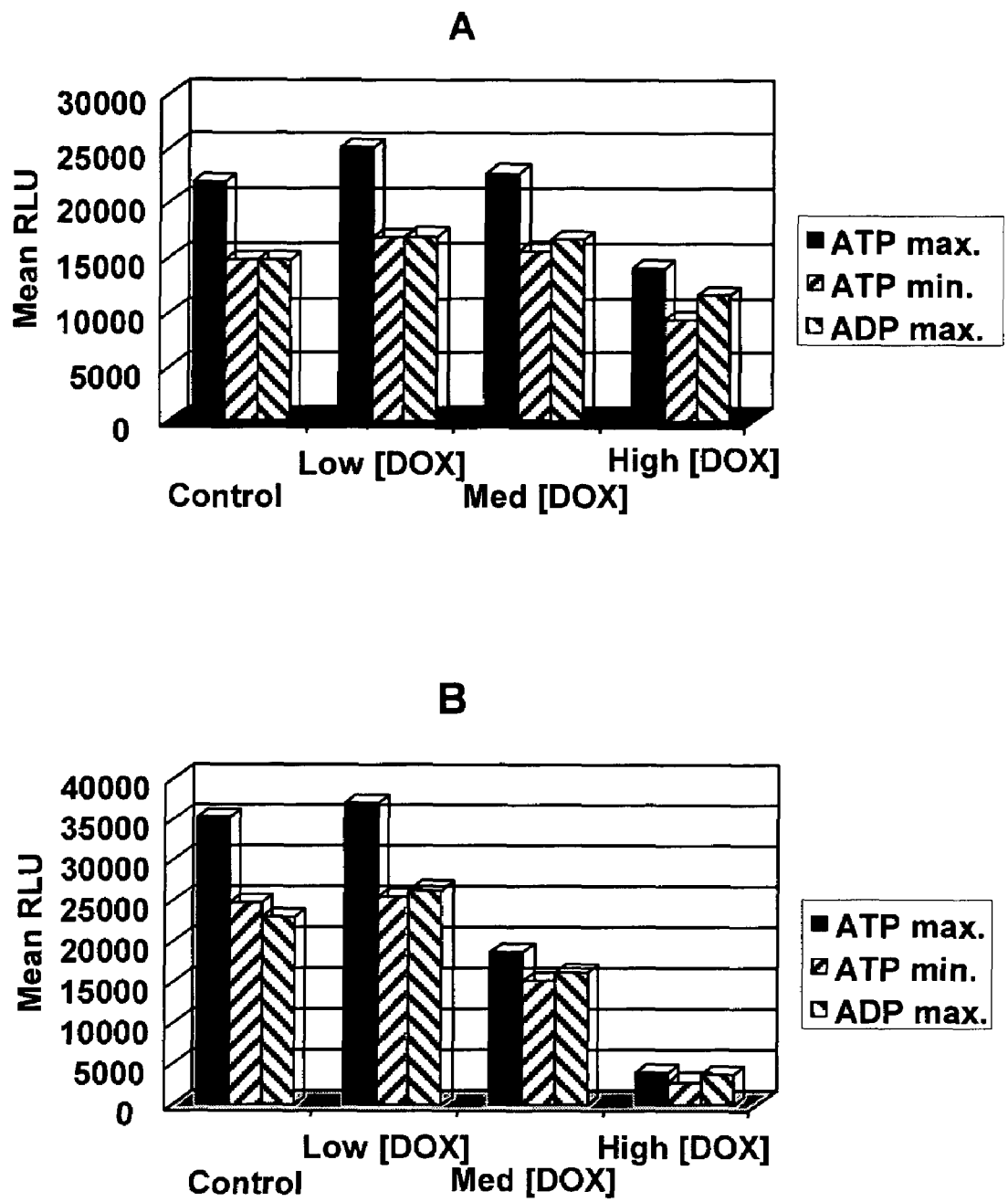
FIGS. 15A and 15B show the mean RLU values for each of the DOX concentrations on peripheral blood mononuclear cells measured at day 3 (FIG. 15A) and day 7 (FIG. 15B).
Figure 16:
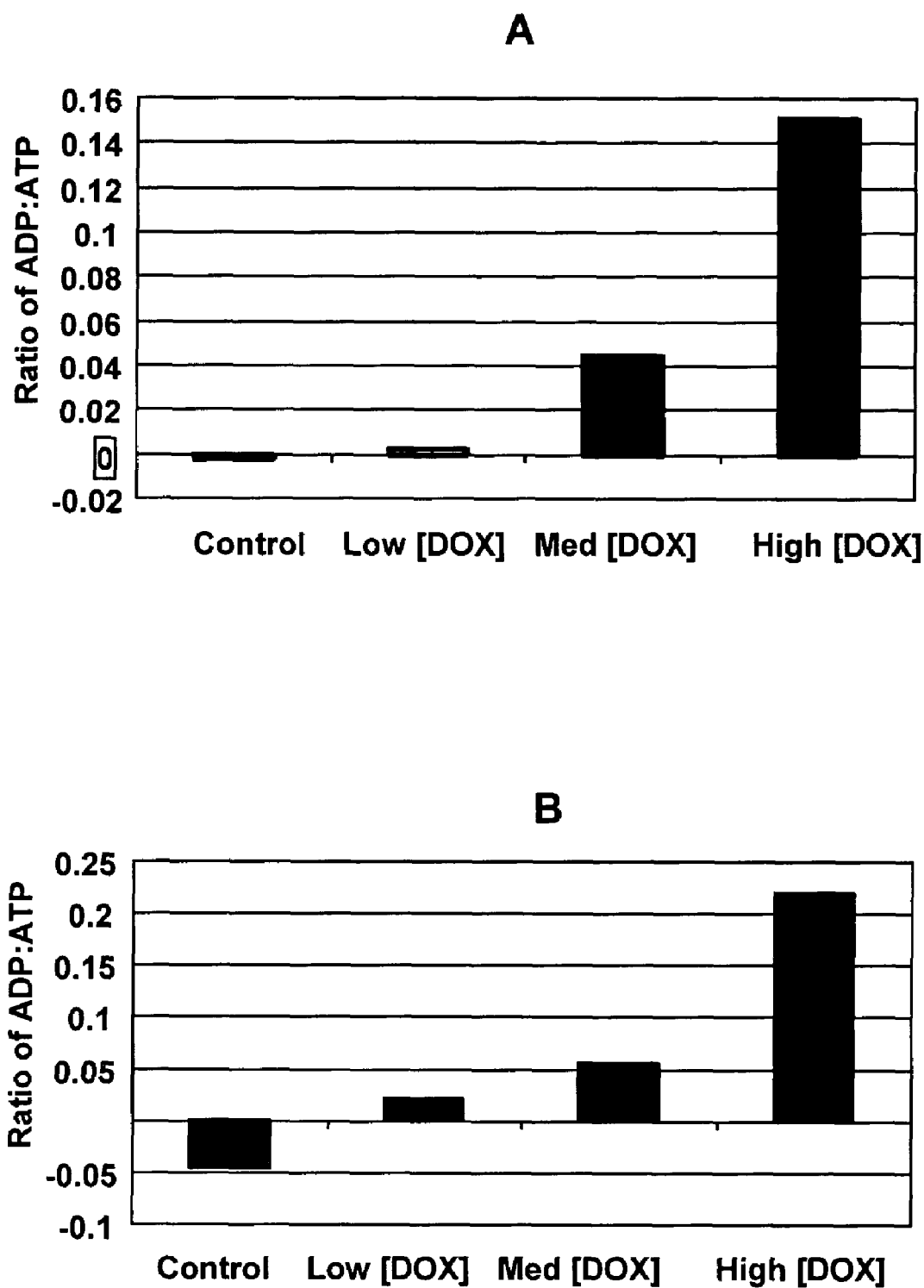
FIGS. 16A and 16B show the effect of DOX on the ADP:ATP ratio of peripheral blood mononuclear cells at day 3 (FIG. 16A) and day 7 (FIG. 16B).

Cell proliferation and apoptosis can actually be performed in a single read by performing HALO as described above, but then instead of measuring only ATP, adenosine diphosphate (ADP) is also measured, as shown in FIGS. 15 and 16. The ratio of ADP:ATP provides a determination of apoptosis. More precisely, the ADP:ATP ratio differentiates between necrosis and apoptosis. If cells are stimulated, ATP levels will increase with no change in the ADP levels. Cell proliferation is indicated. Since apoptosis is an energy-requiring process, ATP is essential for many of the early events of apoptosis. When ATP levels decline to a point where basic metabolic function can no longer process, the cells will die. When apoptosis is initiated, the decline in ATP compared to control values, is followed by an increase in ADP levels without any further increase in ATP concentrations. Thus, the ADP:ATP ratio increases. In primary necrosis, ATP levels rapidly decline with a concomitant and drastic increase in ADP levels. The extreme increase in ADP indicates necrosis.

In the HALO methods that form the basis of the kits of the present invention, ATP is released from the cells using ATP releasing reagent and a 15 min incubation. Thereafter, the ATP luminescence-monitoring reagent is added and the plates read immediately. Thirty minutes later, an ADP converting reagent (ADP-CR) is added which converts ATP to ADP and the plates are read every 5 mins for a further 15-20 mins. Three values are then used to calculate the kinetics of the reaction. The first reading (A) is that immediately after addition of ATP luminescence-monitoring reagent. The second reading (B) is just prior to addition of ADP-CR, when the decline in ATP is maximal. The third reading (C) is taken at a time when the conversion of ADP to ATP has reached a plateau. The ADP:ATP ratio is then calculated from the simple equation: (C-B)/A. This procedure was performed to obtain the results shown in FIG. 16. The procedure is preferably performed by the automatic addition of ATP luminescence-monitoring reagent and ADP-CR using a luminometer equipped with two injectors.

EXAMPLE 13

HALO Kits for 1-4 96-well Luminescent Plates

| Reagent | Contents | State shipped/ State stored until use | No. of containers | Volume provided |
|---|---|---|---|---|
| Single, 96-well plate kit: | | | | |
| Mix #1 | Serum mix | Sterile, frozen/ frozen | 1 | 7 ml |
| Mix #2 | Methyl cellulose mix | Sterile, frozen/ frozen | 1 | 5 ml |
| Mix #3 | Growth factor mix | Sterile, frozen/ frozen | 1 | 1,225 µl |
| Medium | IMDM | Sterile, frozen/ frozen | 1 | 7.5 ml |
| Standard | ATP | Frozen/Frozen | 1 | 220 µl |
| Cell lysis | ATP-Releasing Reagent (ATP releasing reagent) | Cold (4°)/ Cold (4°) | 1 | 7.4 ml |
| Luminescence | ATP- Monitoring Reagent (ATP luminescence- monitoring reagent)* | Frozen/ Cold (4°) | 1 | 14.8 ml |
| Adhesive plate covering | — | — | 1 | — |
| 96-well plate | Luminescence plate | Individually wrapped | 2 | — |
| | Kit manual | — | 1 | — |
| Two, 96-well plate kit: | | | | |
| Mix #1 | Serum mix | Sterile, frozen/ frozen | 1 | 14 ml |
| Mix #2 | Methyl cellulose mix | Sterile, frozen/ frozen | 1 | 10 ml |
| Mix #3 | Growth factor mix | Sterile, frozen/ frozen | 1 (single populations) | 2450 µl each |
| | | | 2 (dual populations) | 1225 µl each |
| | | | 4 (quad populations) | 310 µl each |
| Medium | IMDM | Sterile, frozen/ frozen | 2 | 10 ml each |
| Standard | ATP | Frozen/Frozen | 1 | 450 µl |
| Cell lysis | ATP- Releasing Reagent (ATP releasing reagent | Cold (4°)/ Cold (4°) | 2 | 14.4 ml |

-continued

| Reagent | Contents | State shipped/ State stored until use | No. of containers | Volume provided |
|---|---|---|---|---|
| Luminescence | ATP-Monitoring Reagent (ATP luminescence-monitoring reagent)* | Frozen/ Frozen | 2 | 28.6 ml |
| Adhesive plate covering | — | — | 2 | — |
| 96-well plate | Luminescence plate | Individually wrapped | 3 | — |
|  | Kit manual | — | 1 | — |
| Three, 96-well plate kit: | | | | |
| Mix #1 | Serum mix | Sterile, frozen/ frozen | 1 | 21 ml |
| Mix #2 | Methyl cellulose mix | Sterile, frozen/ frozen | 1 | 15 ml |
| Mix #3 | Growth factor mix | Sterile, frozen/ frozen | 3 (triple populations) | 1225 μl each |
| Medium | IMDM | Sterile, frozen/ frozen | 2 | 10 ml each |
| Standard | ATP | Frozen/Frozen | 1 | 660 μl |
| Cell lysis | ATP-Releasing Reagent (ATP releasing reagent) | Cold (4°)/ Cold (4°) | 2 | 21.2 ml |
| Luminescence | ATP-Monitoring Reagent (ATP luminescence-monitoring reagent)* | Frozen/ Frozen | 2 | 43.2 ml |
| Adhesive plate covering | — | — | 3 | — |
| 96-well plate | Luminescence plate | Individually wrapped | 5 | — |
|  | Kit manual | — | 1 | — |
| Four, 96-well plate kit: | | | | |
| Mix #1 | Serum mix | Sterile, frozen/ frozen | 2 | 28 ml |
| Mix #2 | Methyl cellulose mix | Sterile, frozen/ frozen | 2 | 20 ml |
| Mix #3 | Growth factor mix | Sterile, frozen/ frozen | 2–8 | Depends on kit type |
| Medium | IMDM | Sterile, frozen/ frozen | 1 | |
| Standard | ATP | Frozen/Frozen | 2 | 440 μl each |
| Cell lysis | ATP-Releasing Reagent (ATP releasing reagent) | Cold (4°)/ Cold (4°) | 3 | 29 ml |
| Luminescence | ATP-Monitoring Reagent (ATP luminescence-monitoring reagent)* | Frozen/ Frozen | 4 | 56 ml |
| Adhesive plate covering | — | — | 4 | — |
| 96-well plate | Luminescence plate | Individually wrapped | 6 | — |
|  | Kit manual | — | 1 | — |

*The ATP luminescence-monitoring reagent should not be thawed until needed and should not be re-frozen once thawed. This reagent is light sensitive. Keep in the dark.

What is claimed is:

1. A high-throughput system for rapidly determining the proliferative status of primitive hematopoietic cells by luminescence output comprising:
   a. a target cell population of mononuclear cells comprising primitive hematopoietic cells;
   b. a medium comprising serum and methyl cellulose;
   c. a proliferation agent specific for a single subpopulation of primitive hematopoietic cells, the proliferation agent comprising one or more growth factors, one or more cytokines, or combinations thereof;
   d. a reagent capable of reacting with ATP and generating luminescence in the presence of ATP; and
   e. a plate;
   wherein the target cell population, the medium, the proliferation agent, and the reagent capable of reacting with ATP are combined in an order to determine the proliferative status of the subpopulation of primitive hematopoietic cells by detecting the level of luminescence generated from the reagent that reacted with the ATP, and
   wherein the level of luminescence detected indicates the amount of ATP in the subpopulation of primitive hematopoietic cells, and the amount of ATP in the subpopulation of primitive hematopoietic cells indicates the proliferative status of the subpopulation of primitive hematopoietic cells.

2. The system of claim 1, wherein the proliferation agent is further selected from the group consisting of erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor, and combinations thereof.

3. The system of claim 2, further comprising instructions for determining the proliferative status of the subpopulation of primitive hematopoietic cells by luminescence output.

4. The system of claim 3, wherein the target cell population of mononuclear cells further comprises a population of human or animal hematopoietic cells.

5. The system of claim 3, further comprising an ATP standard solution.

6. The system of claim 4, wherein the serum further comprises bovine serum albumin, an insulin, an iron-saturated transferrin, and Iscove's modified Dulbecco's medium (IMDM).

7. The system of claim 6, wherein the insulin is recombinant insulin.

8. The system of claim 1 further comprising:
   a. the medium having a concentration of fetal bovine serum between 0% to about 30% by volume;
   b. the methyl cellulose having a concentration of between about 0.4% to about 0.7%, by weight;
   c. an atmosphere having a concentration of oxygen between about 3.5% oxygen and about 7.5% oxygen by volume; and
   d. instructions for determining the luminescence generated by the reagent capable of reacting with ATP and generating luminescence in the presence of ATP.

9. The system of claim 1, wherein the proliferation agent is selected from the group consisting of erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor, and combinations thereof.

10. The system of claim 8, wherein the concentration of fetal bovine serum in the medium is between 0% and about 10% by volume.

11. The system of claim 8, wherein the concentration of methyl cellulose in the medium is about 0.7% by weight.

12. The system of claim 8, wherein the concentration of oxygen in the atmosphere is about 5% by volume.

13. The system of claim 8, wherein the target cell population further comprises an enriched population of hematopoietic stem cells.

14. The system of claim 8, wherein the target cell population further comprises a population enriched in at least one hematopoietic progenitor cell lineage.

15. The system of claim 8, wherein the target cell population further comprises hematopoietic stem cells.

16. The system of claim 8, wherein the target cell population further comprises hematopoietic progenitor cells.

17. The system of claim 8, wherein the target cell population further comprises hematopoietic stem cells and hematopoietic progenitor cells.

18. The system of claim 8, wherein the target cell population further comprises primary hematopoietic cells.

19. The system of claim 18, wherein the primary hematopoietic cells are isolated from an animal tissue selected from the group consisting of peripheral blood, bone marrow, umbilical cord blood, yolk sac, fetal liver, and spleen.

20. The system of claim 19, wherein the animal tissue is obtained from a human.

21. The system of claim 19, wherein the animal tissue is obtained from a mammal.

22. The system of claim 21, wherein the mammal is selected from the group consisting of cow, sheep, pig, horse, goat, dog, cat, non-human primates, rodents, rabbit, and hare.

23. The system of claim 18, wherein the primary hematopoietic cells are isolated from peripheral blood.

24. The system of claim 8, wherein the target cell population further comprises a differentially distinguishable subpopulation of primitive hematopoietic cells, wherein the differentially distinguishable subpopulation of primitive hematopoietic cells is defined by a cell surface marker thereon.

25. The system of claim 24, further comprising:
   a. a cell surface marker indicator capable of selectively binding to a cell surface marker on the differentially distinguishable subpopulation of primitive hematopoietic cells; and
   b. instructions for selectively isolating the differentially distinguishable subpopulation of primitive hematopoietic cells binding the indicator.

26. The system of claim 24, wherein the cell surface marker is CD34.

27. The system of claim 24, wherein the cell surface marker is selected from the group consisting of CD3, CD4, CD8, CD34, CD90 (Thy-1) antigen, CD117, CD38, CD56, CD61, CD41, glycophorin A, HLA-DR, and CD133.

28. The system of claim 25, wherein a magnetic bead separation system is used to selectively isolate the differentially distinguishable subpopulation of primitive hematopoietic cells.

29. The system of claim 25, wherein a flow cytometry and cell sorting apparatus is used to selectively isolate the differentially distinguishable subpopulation of primitive hematopoietic cells.

30. The system of claim 8, wherein the single subpopulation of primitive hematopoietic cells comprises a stem cell lineage selected from the group consisting of colony-forming cell-blast (CFC-blast), high proliferative potential colony forming cell (HPP-CFC), and colony-forming unit-granulocyte, erythroid, macrophage, megakaryocyte (CFU-GEMM).

31. The system of claim 8, wherein the single subpopulation of primitive hematopoietic cells comprises a hematopoietic progenitor cell lineage selected from the group consisting of granulocyte-macrophage colony-forming cell (GM-CFC), megakaryocyte colony-forming cell (Mk-CFC), macrophage colony-forming cell (M-CFC), granulocyte colony forming cell (G-CFC), burst-forming unit erythroid (BFU-E), colony-forming unit-erythroid (CFU-E), colony-forming cell-basophil (CFC-Bas), colony-forming cell-eosinophil (CFC-Eo), B cell colony-forming cell (B-CFC), and T cell colony-forming cell (T-CFC).

32. The system of claim 8, wherein the reagent capable of generating luminescence in the presence of ATP comprises luciferin and luciferase.

33. The system of claim 8, wherein the proliferation agent is further selected from the group consisting of stem cell factor, interleukin-6, Flt3L, and combinations thereof.

34. The system of claim 8, wherein the proliferation agent is further selected from the group consisting of macrophage colony stimulating factor, interleukin-1, interleukin-3, interleukin-6, stem cell factor, and combinations thereof.

35. The system of claim 8, wherein the proliferation agent is further selected from the group consisting of erythropoietin, granulocyte-macrophage colony stimulating factor, granulocyte colony stimulating factor, stem cell factor, interleukin-3, interleukin-6, Flt3L, and combinations thereof.

36. The system of claim 8, wherein the proliferation agent is further selected from the group consisting of (a) erythropoietin, (b) erythropoietin and interleukin-3, (c) erythropoietin and stem cell factor, and (d) erythropoietin, stem cell factor, and interleukin-3.

37. The system of claim 8, wherein the proliferation agent is further selected from the group consisting of (a) granulocyte-macrophage colony stimulating factor, (b) granulocyte-macrophage colony stimulating factor and interleukin-3, and (c) granulocyte-macrophage colony stimulating factor, interleukin-3, and stem cell factor.

38. The system of claim 8, wherein the proliferation agent is further selected from the group consisting of (a) thrombopoietin, and (b) thrombopoietin, interleukin-3, and interleukin-6.

39. The system of claim 8, wherein the proliferation agent is further selected from the group consisting of (a) interleukin-2, and (b) interleukin-7, Flt3L, and interleukin-15.

40. The system of claim 8, wherein the proliferation agent is further selected from the group consisting of (a) interleukin-7, and (b) interleukin-7 and Flt3L.

41. The system of claim 8, wherein the proliferation agent is erythropoietin.

42. The system of claim 8, wherein the proliferation agent is further selected from the group consisting of granulocyte colony stimulating factor and granulocyte-macrophage colony stimulating factor.

43. The system of claim 8, wherein the proliferation agent is further selected from the group consisting of (a) interleukin-3, and (b) interleukin-3 and stem cell factor.

44. The system of claim 8, wherein the proliferation agent is further selected from the group consisting of granulocyte-macrophage colony stimulating factor, interleukin-3, interleukin-5, and combinations thereof.

45. The system of claim 8, wherein the proliferation agent is further selected from the group consisting of (a) macrophage colony stimulating factor, (b) macrophage colony stimulating factor and granulocyte-macrophage colony stimulating factor, and (c) granulocyte-macrophage colony stimulating factor.

46. The system of claim 8, further comprising:
   a. a test compound capable of contacting the target cell population; and
   b. instructions to determine the ability of the test compound to modulate the proliferation of the target cell population.

47. The system of claim 46, further comprising instructions to determine the ability of the test compound to modulate the differentiation of the target cell population.

48. The system of claim 8, wherein the system further comprises:
   a. the target cell population comprising a plurality of target cell subpopulations;
   b. at least one test compound capable of contacting the plurality of target cell subpopulations;
   c. instructions to determine the ability of the at least one test compound to alter the proliferation of the target cell population by comparing the proliferative status of the plurality of target cell subpopulations with the proliferative status of a target population of cells not in contact with the at least one test compound; and
   d. instructions to identify the at least one test compound modulating the proliferative status of the target cell population.

* * * * *